(12) United States Patent
Kunos et al.

(10) Patent No.: US 11,485,709 B2
(45) Date of Patent: *Nov. 1, 2022

(54) CANNABINOID RECEPTOR MEDIATING COMPOUNDS

(71) Applicant: The USA, as represented by the Secretary, Department of Health and Human Services, Bethesda, MD (US)

(72) Inventors: George Kunos, Bethesda, MD (US); Malliga Iyer, Germantown, MD (US); Resat Cinar, Bethesda, MD (US); Kenner C. Rice, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/870,093

(22) Filed: May 8, 2020

(65) Prior Publication Data
US 2020/0331861 A1    Oct. 22, 2020

Related U.S. Application Data

(60) Division of application No. 15/674,365, filed on Aug. 10, 2017, now Pat. No. 10,683,270, which is a continuation of application No. 14/442,383, filed as application No. PCT/US2013/069686 on Nov. 12, 2013, now Pat. No. 9,765,031.

(60) Provisional application No. 61/725,949, filed on Nov. 13, 2012.

(51) Int. Cl.
| | |
|---|---|
| *C07D 231/06* | (2006.01) |
| *C07D 403/12* | (2006.01) |
| *C07D 401/12* | (2006.01) |
| *C07D 409/12* | (2006.01) |
| *C07D 417/12* | (2006.01) |

(52) U.S. Cl.
CPC ......... *C07D 231/06* (2013.01); *C07D 401/12* (2013.01); *C07D 403/12* (2013.01); *C07D 409/12* (2013.01); *C07D 417/12* (2013.01)

(58) Field of Classification Search
CPC .. C07D 231/06; C07D 401/12; C07D 403/12; C07D 409/12; C07D 417/12; A61P 3/04; A61P 3/10; A61P 35/00
See application file for complete search history.

(56) References Cited

U.S. PATENT DOCUMENTS

| | | | |
|---|---|---|---|
| 7,482,470 B2 | 1/2009 | McElroy et al. | |
| 7,666,889 B2 | 2/2010 | McElroy et al. | |
| 8,088,809 B2 | 1/2012 | McElroy et al. | |
| 8,604,060 B2 | 12/2013 | Lotersztajn et al. | |
| 9,765,031 B2 * | 9/2017 | Kunos | C07D 417/12 |
| 10,787,419 B2 * | 9/2020 | Kunos | C07D 409/12 |
| 2005/0080125 A1 | 4/2005 | Jochen et al. | |
| 2005/0239859 A2 | 10/2005 | Antel et al. | |
| 2009/0118345 A1 | 5/2009 | McElroy et al. | |
| 2010/0249087 A1 | 9/2010 | Wang et al. | |
| 2010/0292273 A1 | 11/2010 | Receveur et al. | |
| 2012/0157414 A1 | 6/2012 | McElroy et al. | |
| 2016/0039766 A1 | 2/2016 | Kunos et al. | |
| 2016/0257654 A1 | 9/2016 | Kunos et al. | |
| 2018/0022705 A1 | 1/2018 | Kunos et al. | |
| 2018/0179163 A1 | 6/2018 | Kunos et al. | |
| 2018/0273485 A1 | 9/2018 | Kunos et al. | |

FOREIGN PATENT DOCUMENTS

| | | | |
|---|---|---|---|
| WO | WO 2001/070700 | 9/2001 | |
| WO | WO 02/076949 | 10/2002 | |
| WO | WO 03/026647 | 4/2003 | |
| WO | WO 2003/026648 | 4/2003 | |
| WO | WO 2005/074920 | 8/2005 | |
| WO | WO 2005/084652 | 9/2005 | |
| WO | WO 06/060192 | 6/2006 | |
| WO | WO 2007/131219 | 11/2007 | |
| WO | WO 2009/059264 | 5/2009 | |
| WO | WO 2011/044370 | 4/2011 | |
| WO | WO 2012/068529 | 5/2012 | |
| WO | WO-2012068529 A2 * | 5/2012 | ........... A61K 9/0019 |
| WO | WO 2014/078309 | 5/2014 | |
| WO | WO 2015/172059 | 11/2015 | |
| WO | WO 2016/196646 | 12/2016 | |

OTHER PUBLICATIONS

Huang et al. "Recent advances in the understanding of the role of the endocannabinoid system in liver diseases" Dig. Liver Dis. 2011, 43, 188-193. (Year: 2010).*
Cinar et al., "Hybrid inhibitor of peripheral cannabinoid-1 receptors and inducible nitric oxide synthase mitigates liver fibrosis," *JCI Insight*, 1(11): 38 pages, Jul. 21, 2016.
Final Office Action issued for U.S. Appl. No. 15/061,829 dated Dec. 4, 2017.
Final Office Action issued for U.S. Appl. No. 15/061,829 dated Dec. 6, 2019.
Final Office Action issued for U.S. Appl. No. 15/674,333 dated Dec. 6, 2019.
Gahl et al., "Effect of pirfenidone on the pulmonary fibrosis of Hermansky-Pudlak syndrome," *Molecular Genetics and Metabolism*, vol. 76, pp. 234-242, 2002.
International Search Report and Written Opinion issued for International Application No. PCT/US2013/069686, dated Apr. 2, 2014.
International Search Report and Written Opinion issued for International Application No. PCT/US2017/020250 dated Jun. 19, 2017.
International Search Report and Written Opinion issued for International Application No. PCT/US2016/035291 dated Aug. 9, 2016.
International Search Report and Written Opinion issued for International Application No. PCT/US2015/029946 dated Jul. 28, 2015.

(Continued)

*Primary Examiner* — Amanda L. Aguirre
(74) *Attorney, Agent, or Firm* — Klarquist Sparkman, LLP

(57) ABSTRACT

A compound, or a pharmaceutically acceptable salt or ester thereof, comprising (i) a $CB_1$ receptor mediating scaffold conjugated to (ii) a second therapeutic scaffold.

21 Claims, 11 Drawing Sheets

(56) References Cited

OTHER PUBLICATIONS

Iyer et al., "Design, Synthesis, and Biological Evaluation of Novel, Non-Brain-Penetrant, Hybrid Cannabinoid CB 1 R Inverse Agonist/Inducible Nitric Oxide Synthase (iNOS) Inhibitors for the Treatment of Liver fibrosis," *Journal of Medicinal Chemistry*, 60(3): Jan. 13, 2017.

Lange et al., "Synthesis, Biological Properties, and Molecular Modeling Investigations of Novel 3,4-Diarylpyrazolines as Potent and Selective B1 Cannabinoid Receptor Antagonists," *J. Med. Chem.*, vol. 47, pp. 627-643, 2004.

Muccioli et al., "Latest advances in cannabinoid receptor antagonists and inverse agonists," *Expert Opin. Ther. Patents*, 16(10): 1405-1423, Oct. 2006.

Non-Final Office Action issued by U.S. Patent and Trademark Office for U.S. Appl. No. 15/061,829 dated Mar. 23, 2017.

Non-Final Office Action issued by U.S. Patent and Trademark Office for U.S. Appl. No. 14/442,383 dated Dec. 15, 2016.

Non-Final Office Action issued by U.S. Patent and Trademark Office for U.S. Appl. No. 15/061,829 dated Jul. 23, 2018.

Non-Final Office Action issued by U.S. Patent and Trademark Office for U.S. Appl. No. 15/579,123 dated Dec. 13, 2018.

Non-Final Office Action issued by U.S. Patent and Trademark Office for U.S. Appl. No. 16/438,850 dated Sep. 13, 2019.

Non-Final Office Action issued for U.S. Appl. No. 15/674,333 dated Apr. 8, 2019.

Servettaz et al., "Targeting the Cannabinoid Pathway Limits the Development of Fibrosis and Autoimmunity in a Mouse Model of Systemic Sclerosis," *The American Journal of Pathology*, 177(1): 187-197, Jul. 2010.

STN Reg. No. 505059-59-6, entered Apr. 25, 2003.

Tam et al. "Peripheral Cannabinoid-1 Receptor Inverse Agonism Reduces Obesity by Reversing Leptin Resistance," *Cell Metabolism*, 16: 167-179, Aug. 8, 2012.

Tam et al. "Peripheral CB1 cannabinoid receptor blockade improves cardiometabolic risk in mouse models of obesity," *The Journal of Clinical Investigation*, 120(8): 2953-2966, Aug. 2010.

U.S. Appl. No. 14/442,383, filed May 12, 2015.
U.S. Appl. No. 15/061,829, filed Mar. 4, 2016.
U.S. Appl. No. 15/309,728, filed Nov. 8, 2016.
U.S. Appl. No. 15/579,123, filed Dec. 1, 2017.
U.S. Appl. No. 15/674,333, filed Aug. 10, 2017.
U.S. Appl. No. 15/674,365, filed Aug. 10, 2017.

\* cited by examiner

Compound V

Compound V iNOS inhibitor screening
Tissue homogenate
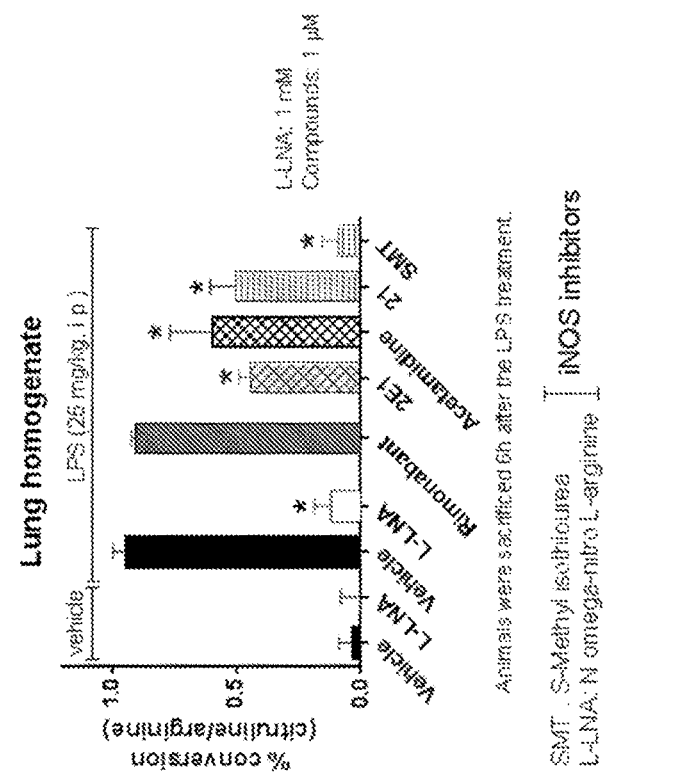
RAW 264.7 Cells#
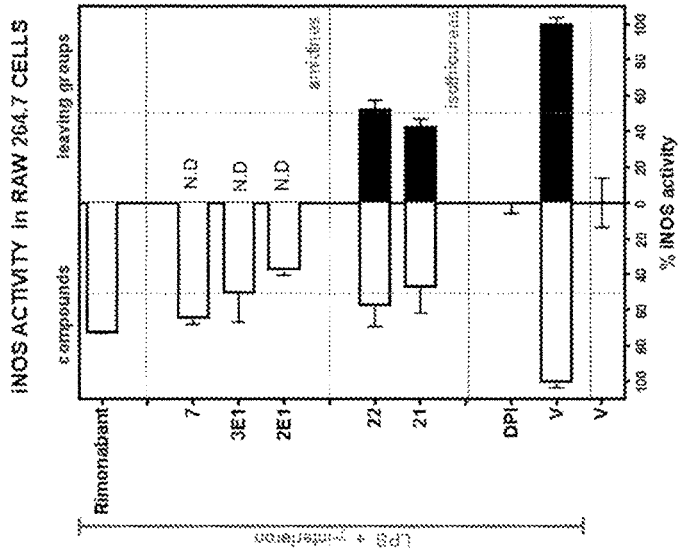

Anti-obesity effect

Body weight

Cumulative food intake

Serum leptin level

Liver-TG

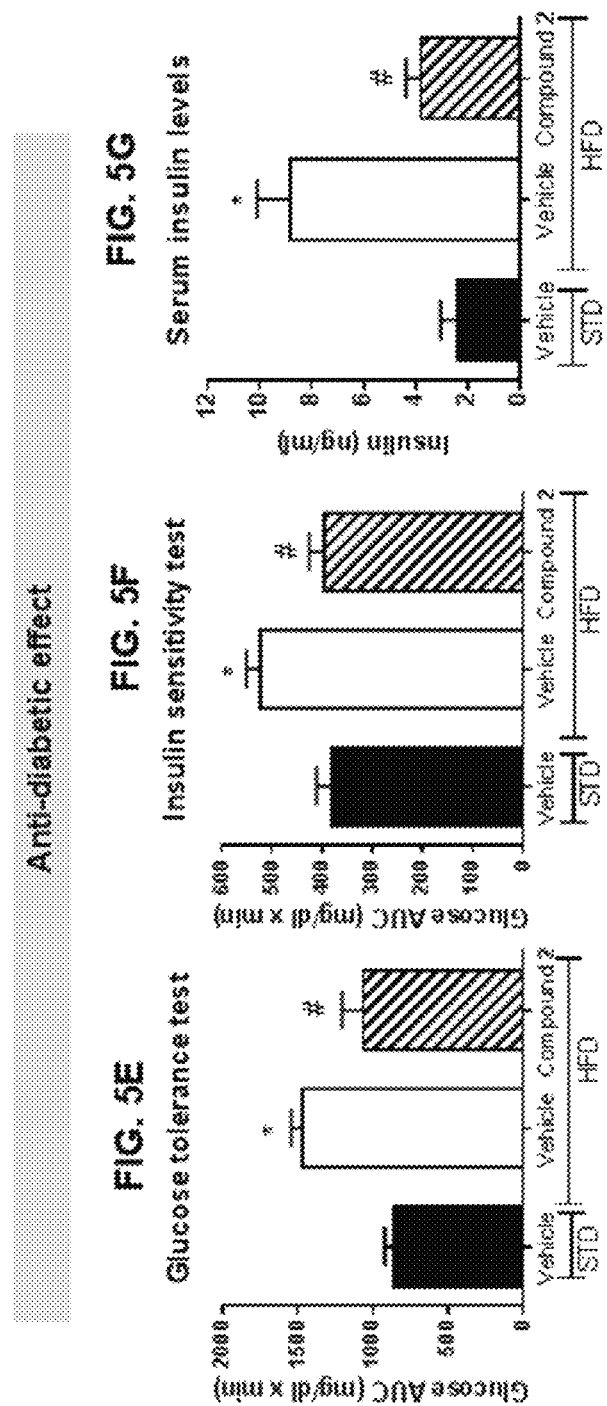

CANNABINOID RECEPTOR MEDIATING COMPOUNDS

CROSS-REFERENCE TO RELATED APPLICATIONS

This application is a divisional of U.S. application Ser. No. 15/674,365, filed Aug. 10, 2017, which is a continuation of U.S. application Ser. No. 14/442,383, filed May 12, 2015, issued as U.S. Pat. No. 9,765,031 on Sep. 19, 2017, which is the U.S. National Stage of International Application No. PCT/US2013/069686, filed Nov. 12, 2013, which claims the benefit of U.S. Provisional Application No. 61/725,949, filed Nov. 13, 2012, all of which are incorporated herein in their entirety.

BACKGROUND

Endocannabinoids are lipid signaling molecules that act on the same cannabinoid receptors—$CB_1$ and $CB_2$—that recognize and mediate the effects of marijuana. Activation of $CB_1$ receptors increases appetite, increases the biosynthesis and storage of lipids, inhibits the actions of insulin and leptin, and promotes inflammation and fibrosis, which has led to the development of $CB_1$ receptor blocking drugs for the treatment of obesity and its metabolic complications, referred to as the metabolic syndrome. The prototype compound rimonabant proved effective in the treatment of the metabolic syndrome, but caused neuropsychiatric side effects, which resulted in its withdrawal from the market and halted further therapeutic development of this class of compounds.

SUMMARY OF THE DISCLOSURE

In one embodiment, there is disclosed herein a compound, or a pharmaceutically acceptable salt or ester thereof, having a structure of:

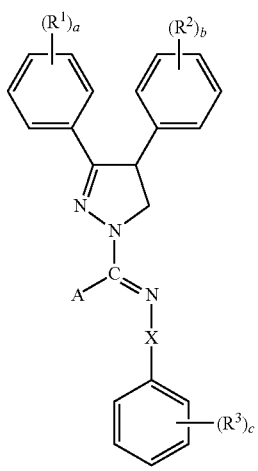

Formula I wherein A is an amidino-containing moiety, a hydrazino-containing moiety,

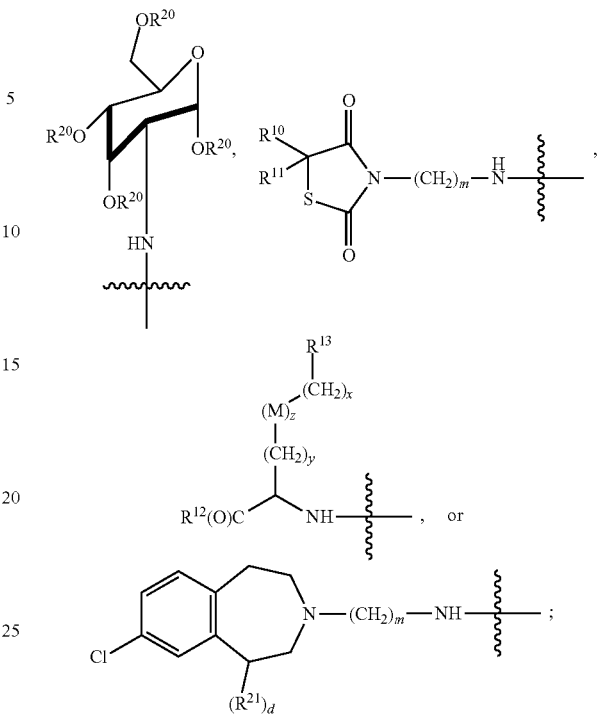

$R^1$, $R^2$, and $R^3$ are each independently selected from optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

X is $SO_2$ or C=O;

$R^{10}$, $R^{11}$, $R^{12}$, $R^{13}$, and $R^{20}$ are each independently selected from H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

$R^{21}$ is optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

M is S or Se;

a, b, and c are each independently 0, 1, 2, 3, 4 or 5;

m, x, and y are each independently 0, 1, 2, 3, 4, 5 or 6;

d is 0 or 1; and z is 1 or 2.

Disclosed herein in a further embodiment is a compound, or a pharmaceutically acceptable salt or ester thereof, comprising (i) a $CB_1$ receptor mediating scaffold and (ii) a second therapeutic scaffold.

Also disclosed herein is a compound, or a pharmaceutically acceptable salt or ester thereof, having a structure of:

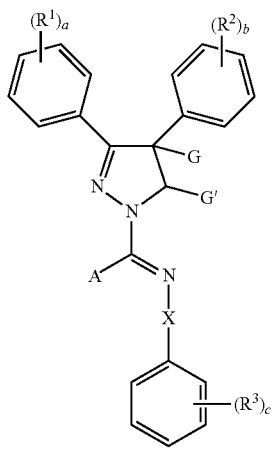

Formula II wherein A is an amidino-containing moiety, a hydrazino-containing moiety, an optionally-substituted thiol,

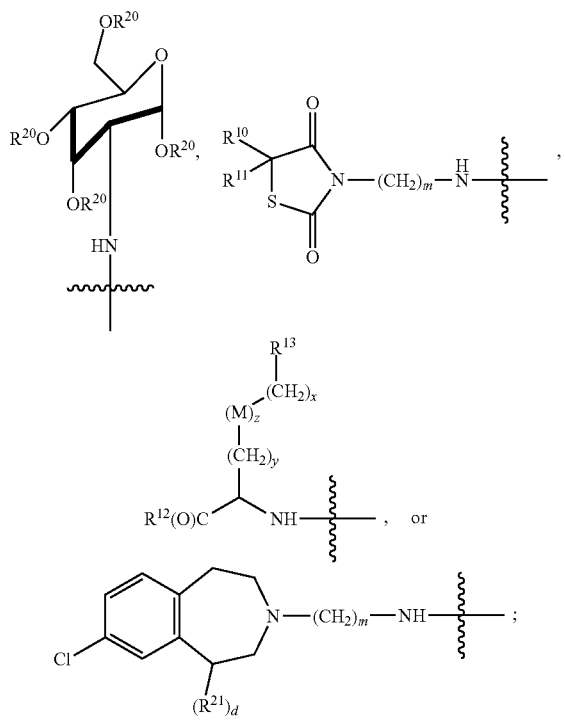

$R^1$, $R^2$, and $R^3$ are each independently selected from optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

G and G' are each independently H, hydroxy, optionally-substituted alkyl, aralkyl, amino, or optionally-substituted thiol;

X is $SO_2$ or C=O;

$R^{10}$, $R^{11}$, $R^{12}$, $R^{13}$, and $R^{20}$ are each independently selected from H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

$R^{21}$ is optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

M is S or Se;

a, b, and c are each independently 0, 1, 2, 3, 4 or 5;

m, x, and y are each independently 0, 1, 2, 3, 4, 5 or 6;

d is 0 or 1; and z is 1 or 2.

Disclosed herein in a further embodiment is a pharmaceutical composition comprising a compound disclosed herein, and at least one pharmaceutically acceptable additive.

Disclosed herein in a further embodiment is a method for treating obesity, diabetes, non-alcoholic and alcoholic fatty liver disease, or a co-morbidity of obesity such as arteriosclerotic heart disease or gout, in a subject, comprising administering to the subject in need thereof a therapeutically effective amount of a compound disclosed herein.

Disclosed herein in a further embodiment is a method for treating fibrosis or liver cancer in a subject, comprising administering to the subject in need thereof a therapeutically effective amount of a compound disclosed herein.

Disclosed herein in a further embodiment is a method of preventing or reversing the deposition of adipose tissue in a subject, comprising administering to the subject in need thereof an effective amount of a compound disclosed herein.

The foregoing will become more apparent from the following detailed description of a several embodiments which proceeds with reference to the accompanying figures.

BRIEF DESCRIPTION OF THE FIGURES

FIG. 4 shows iNOS inhibitory effect of compounds disclosed herein. #RAW264.7 cells incubated for 24 h in the absence or presence of LPS (50 ng/ml) and γ-interferon (10 ng/ml). Cellular iNOS activity was determined after replacing growth medium with reaction mixtures containing appropriate ligands (100 nM). & Mice were treated in vivo with vehicle or LPS (25 mg/kg, ip) and sacrificed 6 h later. Crude homogenate prepared from lung were incubated with the indicated ligands and iNOS activity was determined using a radioactivity-based assay.

FIGS. 5A-5G are graphs showing anti-obesity and anti-diabetic effects for a compound disclosed herein. DIO mice were treated for 14 days with the compound 2 (10 mg/kg/day). Compound 2 treatment reduced body weight (A), food intake (B), hyperleptinemia (C), hepatic TG (D) and abrogated HFD-induced glucose intolerance (E), insulin resistance (F), and hyperinsulinemia (G). Data represent mean±SEM from 5-6 mice per group. *(P<0.05), indicate significant difference from (Pettersen et al.) diet control. #indicates significant treatment effect (P<0.05) relative to vehicle-treated HFD group.

DETAILED DESCRIPTION OF SEVERAL EMBODIMENTS

Terminology

Figure 1:
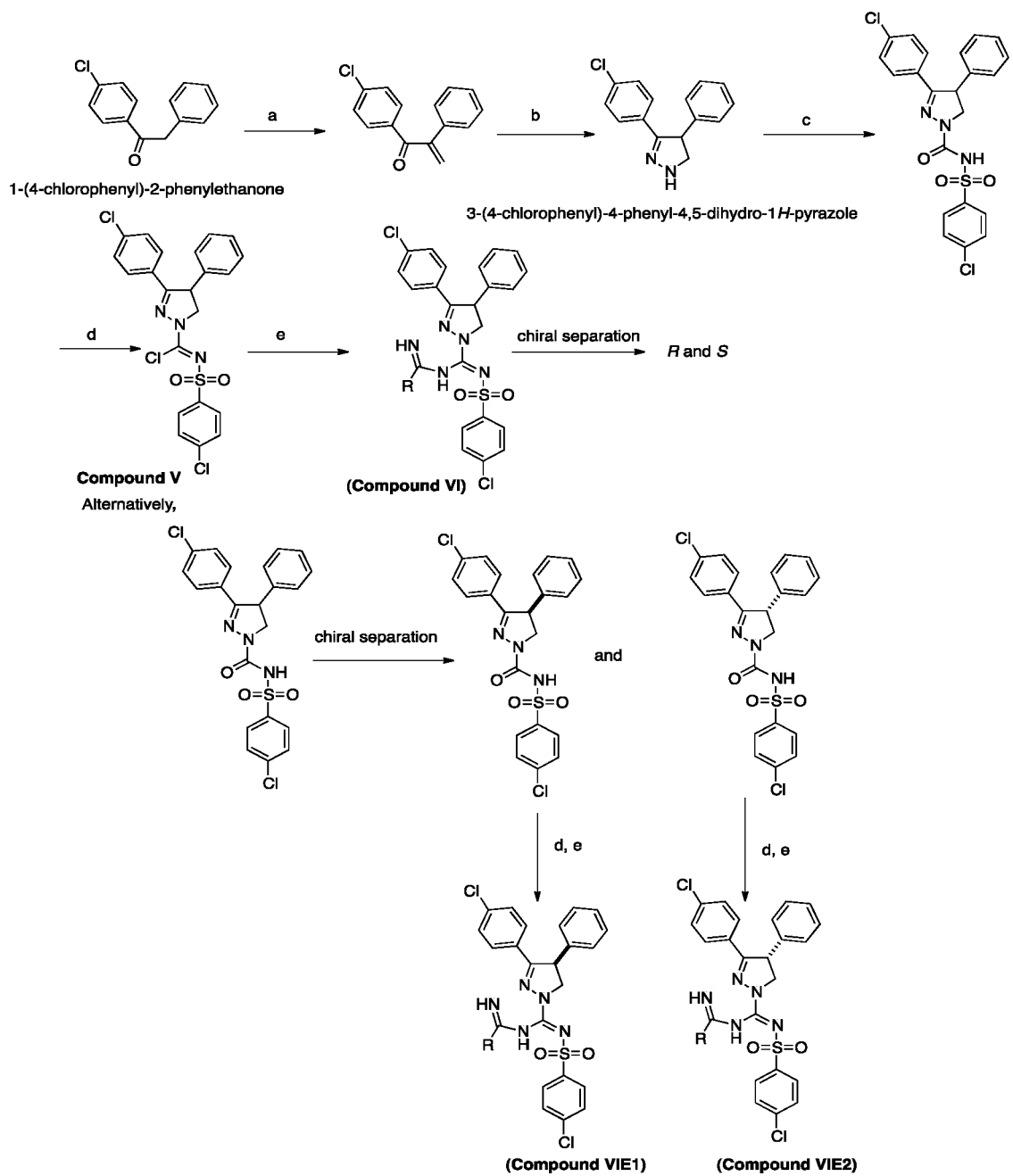
FIGS. 1, 2 and 3 depict synthesis schemes for compounds disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aminoalkyl" refers to alkyl groups as defined above where at least one hydrogen atom is replaced with an amino group (e.g., —$CH_2$—$NH_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

The term "carboxylate" or "carboxyl" refers to the group —$COO^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a dendrimeric compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the dendrimeric platform disclosed herein and/or by covalently conjugating the agents to the surface of the dendrimeric platform.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester (CO$_2$Me), ethylester (CO$_2$Et) and propylester (CO$_2$Pr) and includes reverse esters thereof (e.g. —OCOMe, —OCOEt and —OCOPr).

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_2$-$C_6$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino Unless otherwise defined optionally substituted N-heterocyclics includes pyridinium salts and the N-oxide form of suitable ring nitrogens.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, aryl$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

"Sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —$SO_2$H.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2$Me, —$SO_2$Et and —$SO_2$Pr.

The term "sulfonylamido" or "sulfonamide" refers to the group —$SO_2NH_2$.

A "therapeutically effective amount" refers to a quantity of a specified agent sufficient to achieve a desired effect in a subject being treated with that agent. For example, a therapeutically amount may be an amount of a FBXO3 inhibitor that is sufficient to inhibit inflammation in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Thiol" refers to the group —SH.

The term "substituted thiol" refers to a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits food intake or weight gain in a subject. In certain embodiments disclosed herein, the treatment inhibits fibrogenesis or reverses insulin resistance in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Compounds

Disclosed herein are novel peripherally restricted cannabinoid receptor mediating compounds for the treatment of, for example, fibrosis, diabetes, obesity and liver cancer. The cannabinoid receptor may be $CB_1$ and/or $CB_2$ receptors. The compounds may be essentially non-selective for $CB_1$ versus $CB_2$, or show selectivity for either the $CB_1$ receptor or the $CB_2$ receptor. In a preferred embodiment, the cannabinoid receptor mediating compounds are selective of $CB_1$ receptors.

In certain embodiments, the cannabinoid receptor mediating compounds are cannabinoid receptor inverse agonists, particularly $CB_1$ inverse agonists. In certain embodiments, the cannabinoid receptor mediating compounds are neutral antagonists. A $CB_1$ inverse agonist is a drug that on its own produces an effect opposite to that of a $CB_1$ agonist, and is also able to block the effect of a $CB_1$ agonist. In contrast, a $CB_1$ neutral antagonist can only do the latter (i.e. blocking the effect of a $CB_1$ agonist), but has no effect on its own. $CB_1$ inverse agonism is usually documented by the ability of a drug to decrease GTPgammaS binding and/or to increase adenylate cyclase activity.

In certain embodiments, the compounds preferentially target $CB_1$ receptors in peripheral tissue (e.g., adipose tissue, liver, muscle, lung, kidney, macrophages, pancreatic beta cells and gastrointestinal tract), while not interacting with $CB_1$ receptors in brain tissue. Peripherally-mediated effects are maintained, but CNS side effects are minimal or nonexistent.

Figure 9:
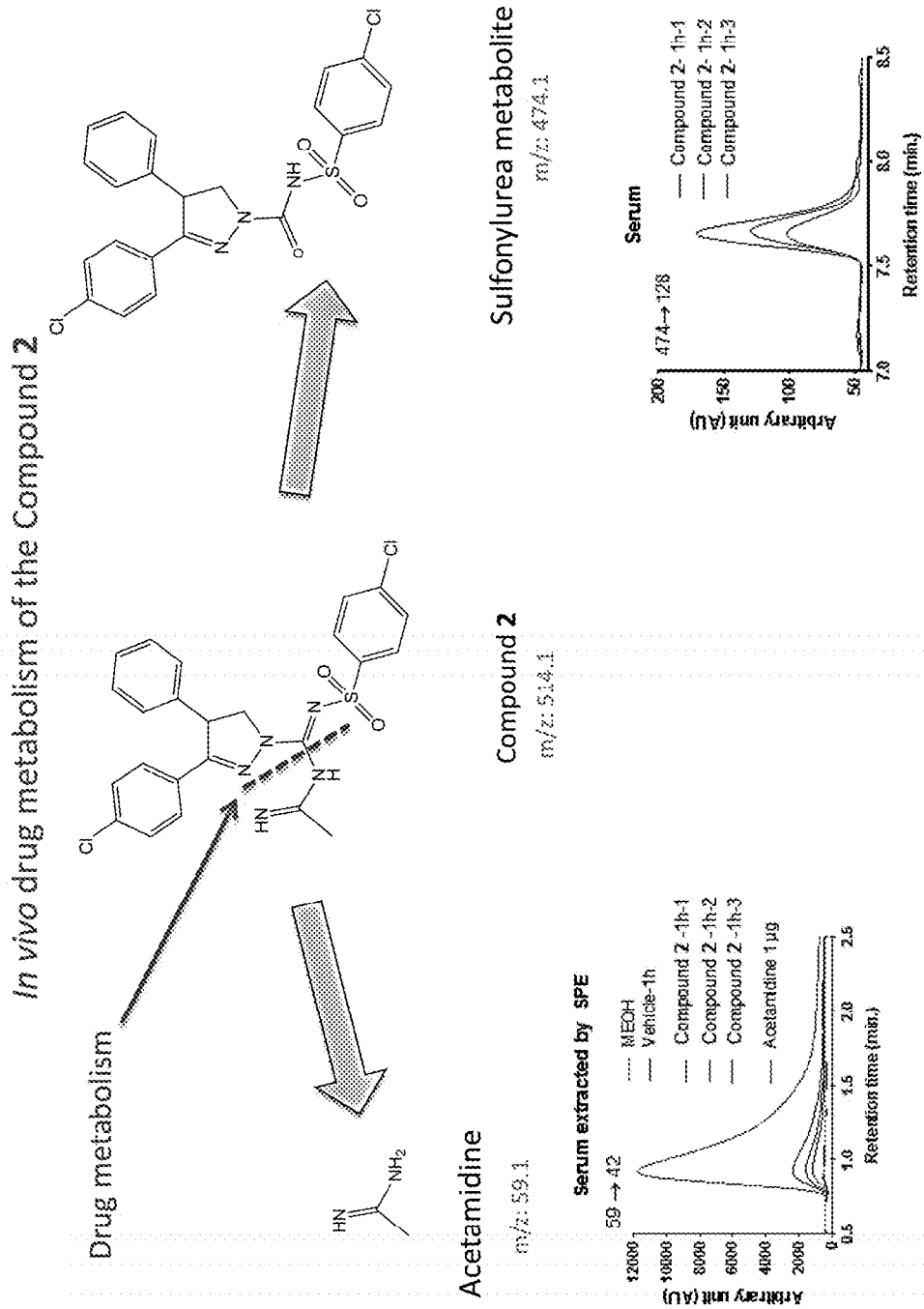
FIG. 9 illustrates the in vivo metabolism of compound 2. A normal mouse was given 10 mg/kg of compound 2 orally and sacrificed 1 h later to analyze the plasma level and chemical structure of the parent compound and its primary metabolites by LC/MS/MS.

There is evidence that the metabolic effects of endocannabinoids are mediated, at least in part, by $CB_1$ receptors in peripheral tissues, whereas the neuropsychiatric side effects are mediated by $CB_1$ receptor in the brain. This suggests $CB_1$ receptor blocking drugs with reduced ability to penetrate the brain would cause fewer if any neuropsychiatric side effects while retaining some or most of their metabolic benefits. As to limited metabolic efficacy of $CB_1$ receptor blocking drugs, this could be improved by the design of dual activity compounds that act on more than one target in the cell to influence the same metabolic process. As an example, such secondary targets could include, but not limited to, the enzyme inducible nitric oxide synthase (iNOS) or adenosine monophosphate kinase (AMPK), as suggested by findings that inhibition of iNOS or activation of AMPK improves insulin resistance, and reduces fibrosis and inflammation (Shinozaki S et al., J. Biol. Chem. 2012, 286(40), 34959-34975; Young R J et al., Bioorg. Med. Chem Let. 2000, 10(6), 597-600; da Silva Morais A et al., Clin. Sci. 2010, 118(6), 411-420). Certain embodiments disclosed herein are $CB_1$ blocking compounds that have very low brain penetrance, and give rise to metabolites that either inhibit iNOS or activate AMPK directly. The generation of an iNOS inhibitory metabolite of compound 2 is illustrated in FIG. 9.

In certain embodiments, a peripherally restricted cannabinoid $CB_1$ receptor mediating compound may be characterized and can be identified from a ratio of maximum concentration in the brain to maximum concentration in plasma which is less than 0.1, as measured in a mouse after intravenous dosing. The preferred peripherally restricted cannabinoid $CB_1$ receptor mediating compounds have a brain $C_{max}$ to plasma $C_{max}$ ratio which is less than 0.05. Especially preferred peripherally restricted cannabinoid receptor mediating compounds have a brain $C_{max}$ to plasma $C_{max}$ ratio which is less than 0.025.

Disclosed herein are compounds, or pharmaceutically acceptable salts or esters, thereof having a formula of:

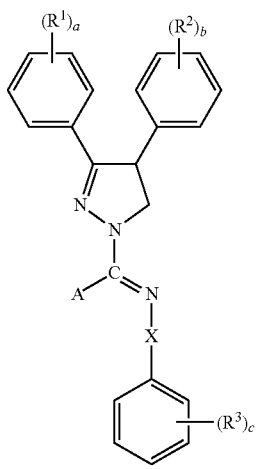

Formula I wherein A is an amidino-containing moiety, a hydrazino-containing moiety,

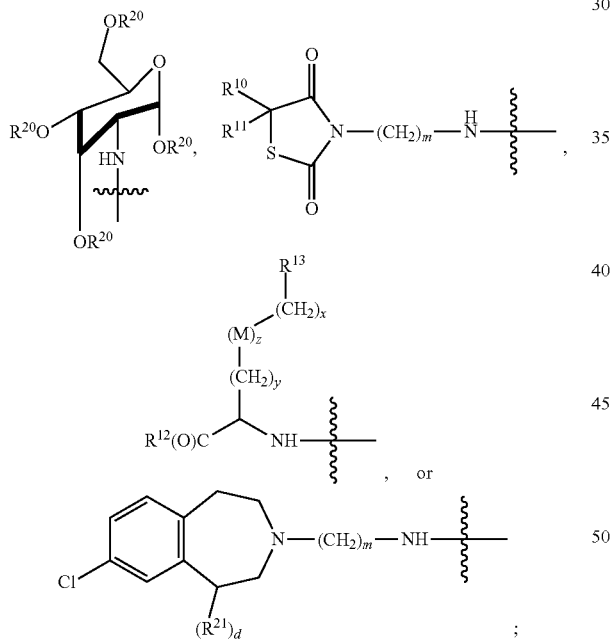

$R^1$, $R^2$, and $R^3$ are each independently selected from optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

X is $SO_2$ or C=O;

$R^{10}$, $R^{11}$, $R^{12}$, $R^{13}$, and $R^{20}$ are each independently selected from H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

$R^{21}$ is optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

M is S or Se;

a, b, and c are each independently 0, 1, 2, 3, 4 or 5;

m, x, and y are each independently 0, 1, 2, 3, 4, 5 or 6;

d is 0 or 1; and z is 1 or 2.

Also disclosed herein is a compound, or a pharmaceutically acceptable salt or ester thereof, having a structure of:

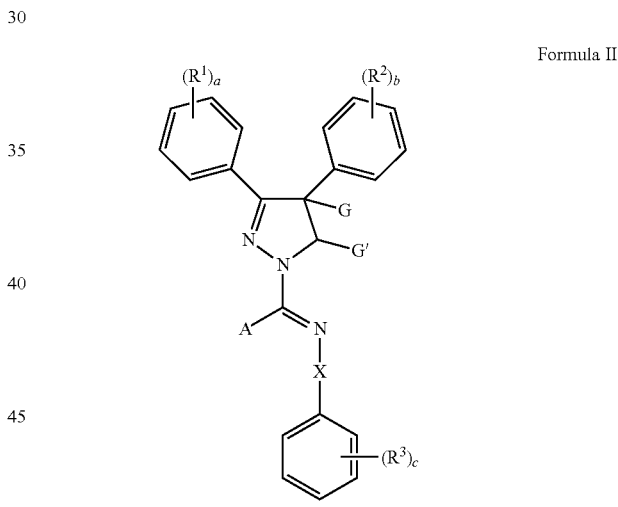

Formula II wherein A is an amidino-containing moiety, a hydrazino-containing moiety, an optionally-substituted thiol,

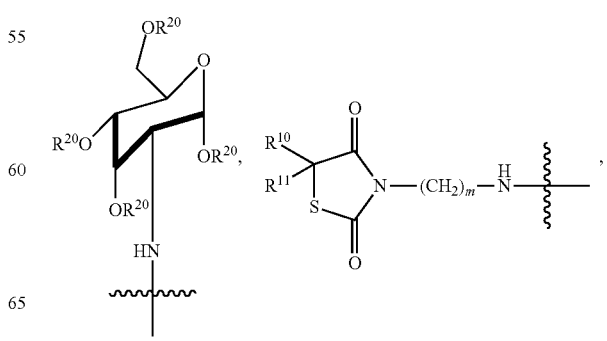

-continued

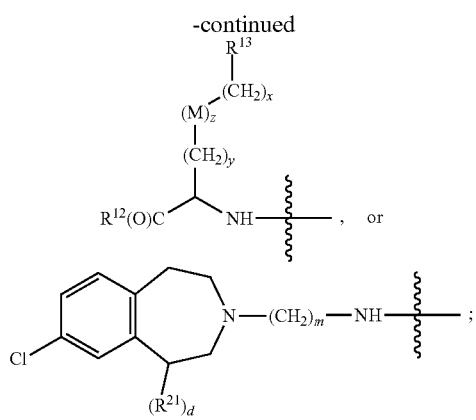

R[1], R[2], and R[3] are each independently selected from optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

G and G' are each independently H, hydroxy, optionally-substituted alkyl, aralkyl, amino, or optionally-substituted thiol;

X is $SO_2$ or C=O;

R[10], R[11], R[12], R[13], and R[20] are each independently selected from H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

R[21] is optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

M is S or Se;

a, b, and c are each independently 0, 1, 2, 3, 4 or 5;

m, x, and y are each independently 0, 1, 2, 3, 4, 5 or 6;

d is 0 or 1; and z is 1 or 2.

In certain embodiments, A is an amidino-containing moiety having a structure of

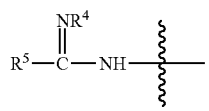

wherein R[4] is selected from H, optionally-substituted alkyl, optionally-substituted cycloalkyl, optionally-substituted heterocycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino; and R[5] is selected from optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino. In certain embodiments, R[5] is an optionally-substituted thiol. In particular embodiments, R[4] is H, hydroxy, $C_1$-$C_6$ alkyl, or acyl (e.g., t-butyloxycarbonyl). In particular embodiments, R[5] is $C_1$-$C_6$ alkyl, $C_3$-$C_6$ cycloalkyl, amino (e.g., —$NH_2$, —N(alkyl)$_2$ or —NH(alkyl)), phenyl, heteroaryl, acyl (e.g., t-butyloxycarbonyl) or heterocycloalkyl. In particular embodiments, R[4] is H, hydroxy, $C_1$-$C_6$ alkyl, or acyl and R[5] is $C_1$-$C_6$ alkyl, $C_3$-$C_6$ cycloalkyl, amino (e.g., —N(alkyl)$_2$ or —NH(alkyl)), phenyl, heteroaryl (e.g., an N-heteroaryl), or heterocycloalkyl (e.g., an N-heterocycloalkyl). In particular embodiments, R[4] is H.

In particular embodiments, R[5] is a thiol substituted with an alkyl (e.g., —S($C_1$-$C_6$ alkyl)), or a substituted alkyl, particularly an aralkyl (e.g, —S($C_1$-$C_6$ alkyl)Ph). In particular embodiments, R[4] is H and R[5] is a substituted thiol.

In particular embodiments, R[5] is an amino of the formula —NR[30]R[31], where R[30] and R[31] can be, independently, hydrogen or an optionally-substituted alkyl, provided that at least one of R[30] and R[31] is optionally substituted alkyl. Illustrative substituted alkyls for R[30] and R[31] include, for example, alkenyl-substituted alkyl, alkoxy-substituted alkyl, aralkyl, heteroaryl-substituted alkyl, cyano-substituted alkyl, cycloalkyl-substituted alkyl, and carboxylate-substituted alkyl. In particular embodiments, R[4] is H, R[30] is H, and R[31] is an optionally-substituted alkyl.

In certain embodiments, the amidino-containing moiety of A is a biguanidino-containing moiety having a structure of

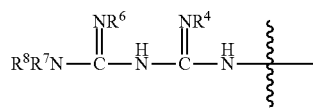

wherein R[4], R[6], R[7], and R[8] are each independently selected from H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino. In particular embodiments, R[4] and R[6] are each H. In particular embodiments, R[7] and R[8] are each independently selected from H or $C_1$-$C_6$alkyl. In particular embodiments, R[4] and R[6] are each H, and R[7] and R[8] are each independently selected from H or $C_1$-$C_6$alkyl.

In certain embodiments, A is a hydrazino-containing moiety has a structure of

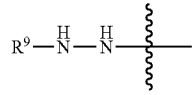

wherein $R^9$ is H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino. In particular embodiments, $R^9$ is H or $C_1$-$C_6$ alkyl.

In certain embodiments, a and c are each one, $R^1$ is halogen (particularly Cl), and $R^3$ is halogen (particularly Cl). In certain embodiments, b is zero.

In certain embodiments, X is $SO_2$.

In certain embodiments, each $R^{20}$ is independently H or $C_1$-$C_6$ alkyl.

In certain embodiments, $R^{10}$ and $R^{11}$ are each independently H or $C_1$-$C_6$ alkyl.

In certain embodiments, $R^{12}$ is H, $C_1$-$C_6$ alkyl, aryl, or amino. In certain embodiments, $R^{13}$ is H or $C_1$-$C_6$ alkyl. In certain embodiments, M is S.

In certain embodiments, A is

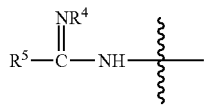

wherein $R^4$ is H, and $R^5$ is $C_1$-$C_6$ alkyl, $C_3$-$C_6$ cycloalkyl, amino (e.g., —N(alkyl)$_2$ or —NH(alkyl)), phenyl, heteroaryl (e.g., an N-heteroaryl), or heterocycloalkyl (e.g., an N-heterocycloalkyl); and X is $SO_2$.

More specific examples of compounds disclosed are listed below. wherein A is as described herein;

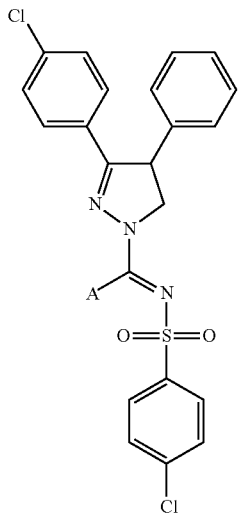

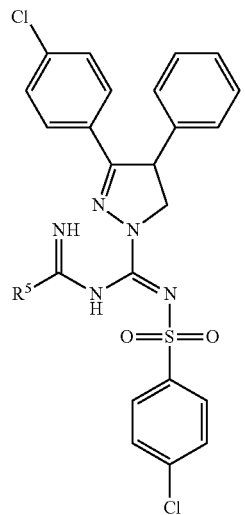

wherein $R^5$ is as described herein.

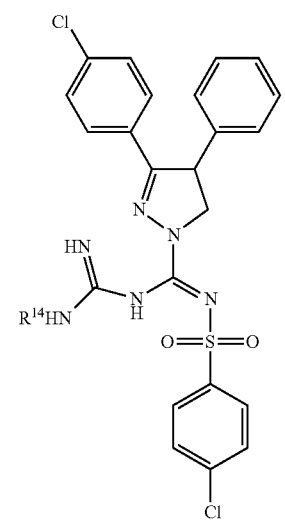

wherein $R^{14}$ is H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino. In certain embodiments, $R^{14}$ is H, acyl, or $C_1$-$C_6$ alkyl.

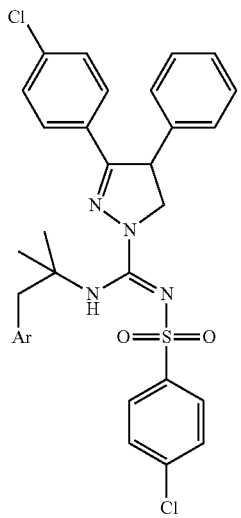

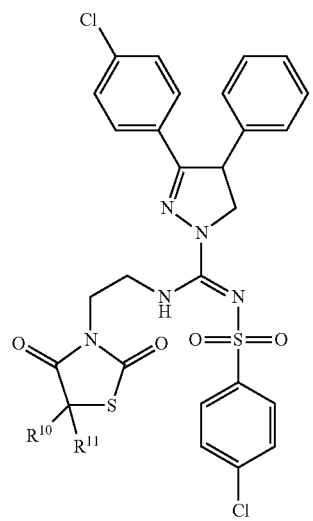

wherein $R^{10}$ and $R^{11}$ are as described herein.

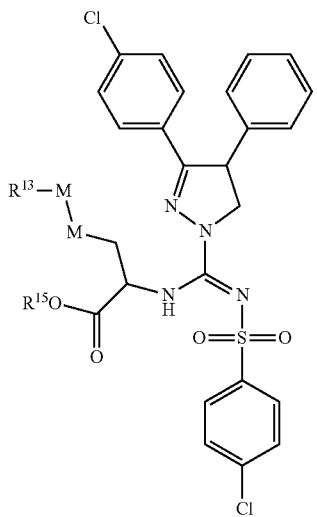

wherein $R^{13}$ is as described herein, and $R^{15}$ is H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino. In certain embodiments, $R^{15}$ is H, $C_1$-$C_6$ alkyl, or amino.

In certain embodiments, at least one of G or G' are hydroxy, optionally-substituted $C_1$-$C_6$ alkyl (e.g., phenyl-substituted $C_1$-$C_6$ alkyl), amino, or alkoxy-substituted thiol having a structure of $S(CH_2)_nR$, where R can be H, alkyl or aralkyl and n is 1 to 10.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

For example, compounds of formula I may be in the form of a stereoisomeric mixture or cis/trans isomers. In certain embodiments, the compounds of formula I may be provided as an S-enantiomer:

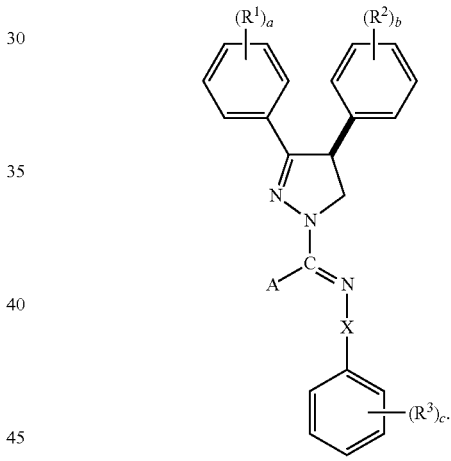

In certain embodiments, the compounds of formula I may be provided as an R-enantiomer:

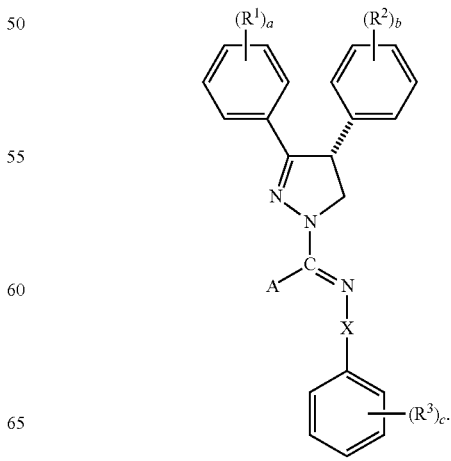

In certain embodiments, the S-enantiomer is preferred. In certain embodiments, the R-enantiomer is preferred.

In certain embodiments, the agents disclosed herein are hybrid compounds that include (i) a $CB_1$ receptor mediating scaffold (e.g., an inverse agonist or neutral antagonist) and (ii) a second therapeutic scaffold. The hybrid compounds may be 3-phenyl-N'-phenyl-N-imino-1H-pyrazole-1-carboximidiamide compounds. In certain embodiments, the "A" moiety in formula I constitutes at least a portion of the second therapeutic scaffold. In certain embodiments, the second therapeutic scaffold may undergo in vivo cleavage, thereby releasing the second therapeutic scaffold which may retain at least a portion of its therapeutic activity. For example, in the case of metformin as the second therapeutic scaffold, the resulting hybrid compound could have therapeutic efficacy not only due to its blockade of $CB_1$ receptors, but also due to the release of metformin, a widely used antidiabetic agent, during the in vivo metabolism of the compound. The in vivo cleavage may occur at any location in the body, but typically occurs in the liver, via the action of drug metabolizing enzymes, such as isoforms of cytochrome P450. In certain embodiments, the cleavage occurs at the bond between the "A" moiety and the C atom of the carboximidiamide portion of the compound.

Illustrative second therapeutic scaffolds include an antidiabetic agent, an anticancer agent, an antiobesity agent, and an antifibrotic agent.

The metformin scaffold is either implicit as shown below (compound 44, Table 1 and 2) or as an explicit attachment at the unsubstituted nitrogen end:

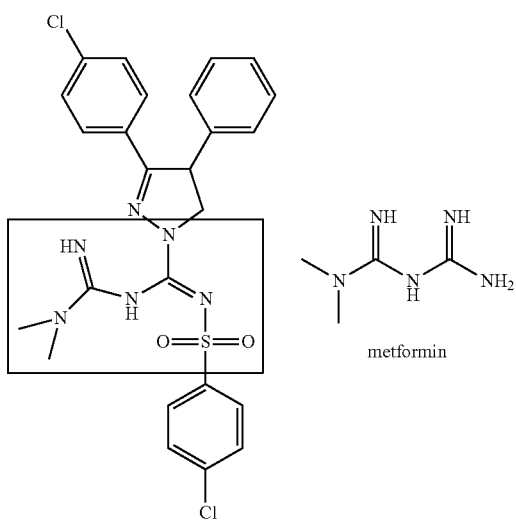

metformin scaffold in compound 44

A further illustrative antidiabetic scaffold is:

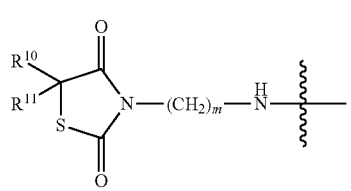

An illustrative anticancer scaffold is:

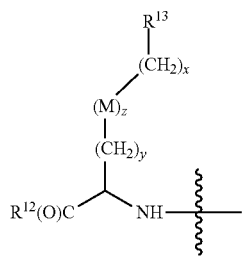

An illustrative antiobesity scaffold is:

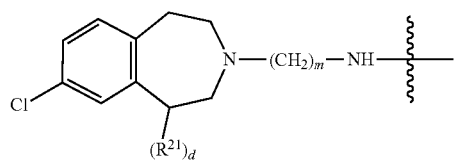

An illustrative iNOS inhibitor scaffold is

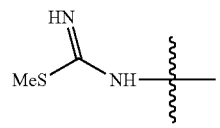

wherein $R^{20}$ is optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino; and d is 0 or 1.

In certain embodiments, the compounds disclosed herein have improved chemical stability resulting in a plasma half-life in the 1-16 hours range, more particularly 4-8 hours range.

In certain embodiments, the compounds disclosed herein have low or no cytochrome P450 activity meaning that the agents may result in few, if any, drug-to-drug interactions.

In certain embodiments, the compounds disclosed herein have a $CB_1R$ binding affinity in the range of 0.1 to 20 nM, and $CB_1/CB_2$ selectivity of at least 20-fold, or more particularly 100-fold or greater.

FIG. 1 depicts a general synthesis method of making the compounds disclosed herein. The method involves chemically linking an amide via an imidoyl chloride to hydrazine-, amidine-, guanidine- or biguanide (e.g., metformin)-containing moieties.

Compositions and Methods of Use

The peripherally restricted cannabinoid receptor mediating agents disclosed herein are unique in that they improve all aspects of the metabolic syndrome. They reduce food intake and body weight, reverse insulin and leptin resistance, reverse hepatic steatosis (fatty liver) and improve dyslipidemia. They may be used for treating obesity, diabetes (e.g., type 2 diabetes), and non-alcoholic and alcoholic fatty liver disease (NAFLD/AFLD), the latter being a risk factor for insulin resistance, cirrhosis and liver cancer, dyslipidemias that predispose to arteriosclerotic heart disease, diabetic nephropathy, gout, and fibrosis. The agents disclosed herein may be devoid of the psychiatric side effects that prevent the use of globally acting CB antagonists.

The diabetes disorder may be Type 1 diabetes, Type 2 diabetes, inadequate glucose tolerance, and/or insulin resistance.

Also disclosed herein is a method for treating a co-morbidity of obesity. The co-morbidity may be selected from diabetes, Metabolic Syndrome, dementia, and heart disease. In further embodiments, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the liver, ovaries, cervix, uterus, breasts, prostrate, and gallbladder.

Also disclosed herein is a method of preventing or reversing the deposition of adipose tissue in a subject. By preventing or reversing the deposition of adipose tissue, the compounds disclosed herein are expected to reduce the incidence or severity of obesity, thereby reducing the incidence or severity of associated co-morbidities.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, an antidiabetic agent, a cholesterol-lowering agent, an anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

FIG. 1 depicts the general route to convert commercially available suitably substituted 2-phenylacetophenones to novel CB1-selective inverse agonist compounds bearing an A appendage as described herein. For example, 1-(4-chlorophenyl)-2-phenylethanone can be converted to 1-(4-chlorophenyl)-2-phenylprop-2-en-1-one using 37% formaldehyde containing piperidine and acetic acid (step a). Treatment of the acrylophenone with hydrazine hydrate in refluxing 2-propanol produces 3-(4-chlorophenyl)-4-phenyl-4,5-dihydro-1H-pyrazole (step b) (J. Agric. Food Chem. 1979, 27, 406). The pyrazoline was condensed with methyl (4-chlorophenyl)sulfonylcarbamate obtained from methyl chloroformate and 4-chlorobenzenesulfonamide to give the diarylpyrazoline acylsulfonamide (step c). Chlorination of this product with phosphorus pentachloride in refluxing chlorobenzene gave the imidoylchloride (step d) as previously described (J. Med CheM. 2004, 47, 627, and Che, Ber. 1966, 99, 2885). The imidoyl chloride was coupled with suitable amidine hydrochloride in (step e) the presence of triethylamine in a mixture of methanol and dichloromethane to yield dihydro-1H-pyrazole-1-carboximidamides. This compound can be subjected to preparative HPLC conditions using a chiral column to give R and S optically pure enantiomers. Alternatively, the racemic diarylpyrazoline acylsulfonamide can be separated on a chiral column to give optically pure enantiomeric acyl sulfonamides which can be individually subjected to further manipulations as shown in step d and e.

Illustrative Example 1

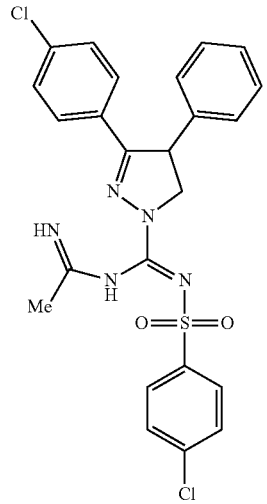 [SMILES: CC(=N)N/C(=N\S(=O)(=O)c1ccc(Cl)cc1)N1CC(c2ccccc2)C(c2ccc(Cl)cc2)=N1]

To the imidoyl chloride compound V (500 mg, 1.02 mmoles) in dichloromethane (10 mL) was added a pre-mixed mixture of acetamidine hydrochloride (3.06 mmoles) in methanol:dichloromethane:Et$_3$N (2:1:1) at −78° C. (step e) dropwise and allowed to warm up to room temperature overnight. The reaction mixture was extracted in to dichloromethane washed with water and purified by flash chromatography using hexanes:EtOAC (6:4) to afford 3-(4-chlorophenyl)-N'-((4-chlorophenyl)sulfonyl)-N-(1-iminoethyl)-4-phenyl-4,5-dihydro-1H-pyrazole-1-carboximidamine in 30-40% yield. The racemic compound was further subjected to chiral preparatory chromatography using (R,R) WhelK-O1 to afford enantiomers E1 and E2. (Analytical: 3.2 min E1, 4.1 min E2 solvent (Hex:DCM:IPA) 40:40:20+0.1% TFA, Flow rate 1 ml/min)

Illustrative Example 2

Figure 2:
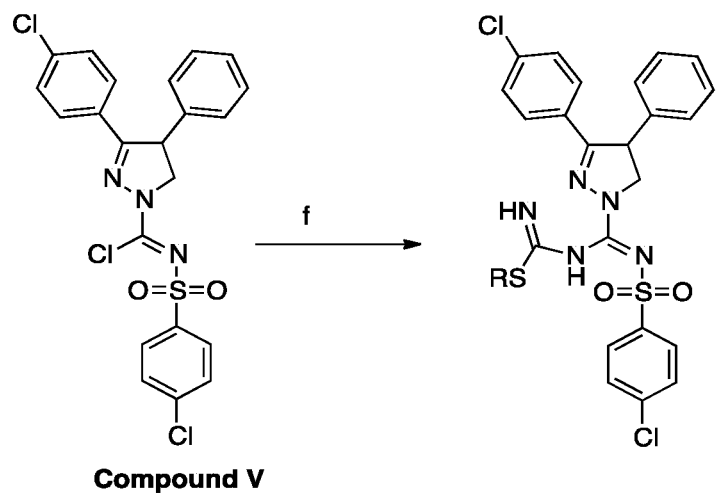

A further synthesis scheme is shown in FIG. 2. For instance, this scheme was used to synthesize

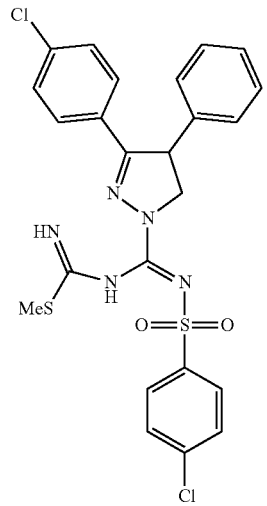 [SMILES: CSC(=N)N/C(=N\S(=O)(=O)c1ccc(Cl)cc1)N1CC(c2ccccc2)C(c2ccc(Cl)cc2)=N1]

To the imidoyl chloride compound V (500 mg, 1.02 mmoles) in dichloromethane (10 mL) was added a pre-mixed mixture of S-methylisothiuronium iodide (2.04 mmoles) in methanol:dichloromethane:Et$_3$N (2:1:1) at −78° C. (step 0 dropwise and allowed to warm up to room temperature overnight. The reaction mixture was extracted in to dichloromethane washed with water and purified by flash chromatography using hexanes:EtOAC (6:4) to afford methyl-((3-(4-chlorophenyl)-4-phenyl-4,5-dihydro-1H-pyrazol-1-yl)(((4-chlorophenyl)sulfonyl)imino)methyl)carbamimidothioate in 35-45% yield.

Illustrative Example 3

Figure 3:
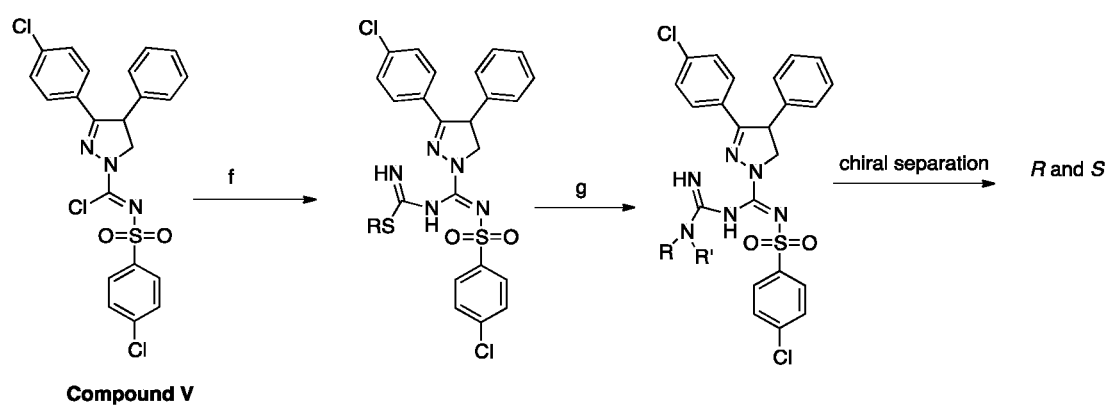

A further synthesis scheme is shown in FIG. 3. For instance, this scheme was used to synthesize

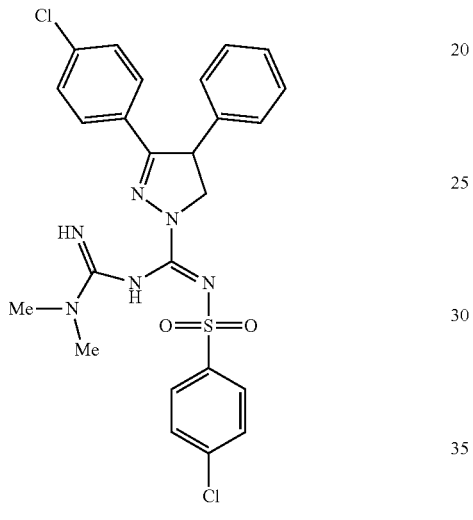

To the imidoyl chloride compound V (100 mg, 0.203 mmoles) in dichloromethane (10 mL) was added a premixed mixture of S-methylisothiuronium iodide (2.04 mmoles) in methanol:dichloromethane:Et$_3$N (2:1:1) (step 0 at −78° C. dropwise and allowed to warm up to room temperature overnight. The reaction mixture was extracted in to dichloromethane washed with water and purified by flash chromatography using hexanes:EtOAC (6:4) to afford the S-methylamidino compound in 35-45% yield. To this compound in CH$_3$CN was added dimethyl amine and pyridine (step g) and heated at 75° C. for 3 h. The reaction mixture was cooled and solvent evaporated. The crude reaction mixture was washed with water extracted in to dichloromethane. The concentrated dichloromethane extract was then purified by Flash chromatography to yield 3-(4-chlorophenyl)-N'-((4-chlorophenyl)sulfonyl)-N—(N,N-dimethylcarbamimidoyl)-4-phenyl-4,5-dihydro-1H-pyrazole-1-carboximidamide in 36% (40 mg) yield over two steps.

Table 1 below summarizes in vitro and in vivo data for several compounds based on the structure:

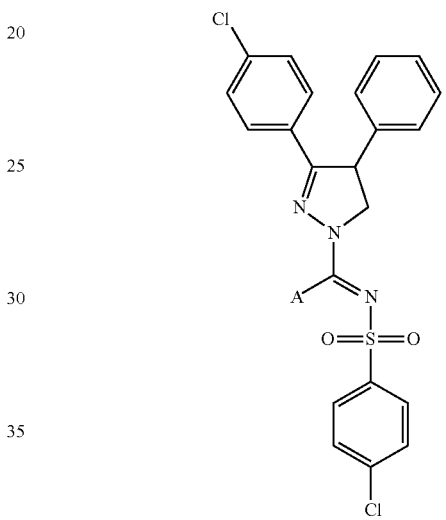

Synthesized Compounds

TABLE 1

| Compound | A | K$_i$ CB$_1$ (nM) | cLogp$^a$ | PSA$^a$ | Brain/ Plasma | Functional GTPγS binding CB$_1$ IC$_{50}$(nM) and E$_{max}$ (% basal) | In vivo Comments |
|---|---|---|---|---|---|---|---|
| 2 | H$_3$C−C(=NH)−NH | 18 | 4.94 | 97.98 | 0.03 | 50 and -20 | -anti-diabetic -anti-obesity |
| 2E1 | H$_3$C−C(=NH)−NH S-enantiomer | 9 | 4.94 | 97.98 | NA | NA | NA |
| 2E2 | H$_3$C−C(=NH)−NH R-enantiomer | 48 | 4.94 | 97.98 | NA | NA | NA |

TABLE 1-continued

Data on synthesized compounds:

| Compound | A | $K_i$ CB$_1$ (nM) | cLogp$^a$ | PSA$^a$ | Brain/ Plasma | Functional GTPγS binding CB$_1$ IC$_{50}$(nM) and E$_{max}$ (% basal) | In vivo Comments |
|---|---|---|---|---|---|---|---|
| 8 | Ph-C(=NH)NH | 26 | 6.79 | 97.98 | NA | NA | NA |
| 41 | BocHN-C(=NH)NH | 6.5 | 6.27 | 136.3 | NA | NA | NA |
| 73 | NH$_2$—NH | 33 | 4.65 | 100.1 | NA | NA | NA |
| Additional compounds: | | | | | | | |
| 12 | 4-pyridyl-C(=NH)NH | 34 | 5.58 | 110.8 | NA | NA | NA |
| 4 | cyclopropyl-C(=NH)NH | 13 | 5.72 | 97.98 | NA | NA | NA |
| 3 | t-Bu-C(=NH)NH | 7 | 6.78 | 97.98 | NA | NA | NA |
| 52 | morpholino-C(=NH)NH | 193 | 4.98 | 110.4 | NA | NA | NA |
| 55 | pyrrolidino-C(=NH)NH | 241 | 5.61 | 101.2 | NA | NA | NA |
| 44 | (CH$_3$)$_2$N-C(=NH)NH | 171 | 5.20 | 101.2 | NA | NA | NA |

$^a$Theoretical values

Compounds disclosed in Table 1 are also shown in Table 2, which includes additional compounds. They were analogously prepared as shown in FIG. 1, FIG. 2 or FIG. 3:

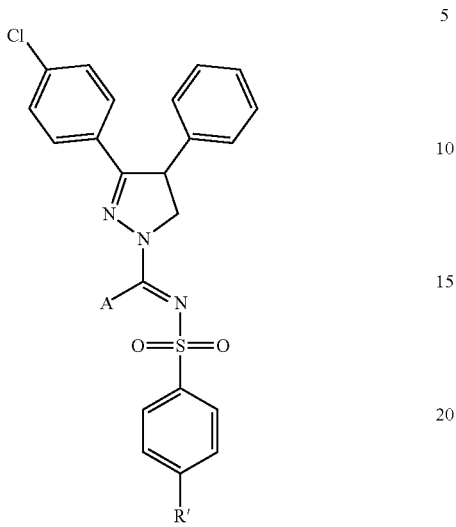

TABLE 2

| Serial # | A | R' | $K_i$ CB$_1$ (nM) | $^1$HNMR | $[M + H]^+$ |
|---|---|---|---|---|---|
| 1 | HN=CH-NH | Cl | 392 | (500 MHz, CDCl$_3$): δ 8.34 (s, 1H), 7.86 (d, J = 7.4 Hz, 2H), 7.52 (d, J = 7.7 Hz, 2H), 7.45 (d, J = 7.5 Hz, 2H), 7.41 (d, J = 7.6 Hz, 3H), 7.30 (d, J = 6.9 Hz, 2H), 7.10 (d, J = 7.2 Hz, 2H), 4.72 (dd, J = 11.5, 5.4 Hz, 1H), 4.39 (t, J = 11.8 Hz, 1H), 4.02-3.98 (m, 1H). | 500.1 |
| 2 | H$_3$C-C(=NH)-NH | Cl | 18 | (500 MHz, CDCl$_3$): δ 7.86 (d, J = 7.8 Hz, 2H), 7.49 (d, J = 7.4 Hz, 2H), 7.27 (d, J = 6.5 Hz, 2H), 7.20-7.18 (m, 3H), 7.07 (d, J = 6.7 Hz, 2H), 6.90-6.88 (m, 2H), 4.71 (dt, J = 6.3, 0.9 Hz, 1H), 4.49 (t, J = 12.0 Hz, 1H), 4.11 (t, J = 6.7 Hz, 1H), 2.04 (s, 3H). | 514.0 |
| 2E1 | H$_3$C-C(=NH)-NH  S-enantiomer | Cl | 9 | — | 514.0 |
| 2E2 | H$_3$C-C(=NH)-NH  R-enantiomer | Cl | 182 | — | 514.0 |
| 3 | (CH$_3$)$_3$C-C(=NH)-NH | Cl | 7 | 500 MHz, CDCl$_3$): δ 7.95 (d, J = 6.6 Hz, 2H), 7.48 (dd, J = 26.1, 8.3 Hz, 2H), 7.36 (d, J = 6.4 Hz, 2H), 7.32 (d, J = 7.1 Hz, 3H), 7.26 (d, J = 8.3 Hz, 2H), 7.20 (s, 2H), 5.52 (d, J = 0.4 Hz, 1H), 4.80 (s, 1H), 4.67 (s, 1H), 4.07 (dd, J = 12.2, 5.8 Hz, 1H), 1.32 (s, 9H). | 556.1 |
| 3E1 | (CH$_3$)$_3$C-C(=NH)-NH  S-enantiomer | Cl | 3.6 | — | 556.1 |

TABLE 2-continued

| Serial # | A | R' | K<sub>i</sub> CB<sub>1</sub> (nM) | $^1$HNMR | [M + H]$^+$ |
|---|---|---|---|---|---|
| 4 | cyclopropyl-C(=NH)NH | Cl | 13 | (500 MHz, CDCl$_3$): δ 7.87 (d, J = 7.8 Hz, 2H), 7.39 (d, J = 8.4 Hz, 2H), 7.28 (d, J = 7.5 Hz, 3H), 7.24 (d, J = 7.4 Hz, 2H), 7.18 (d, J = 8.1 Hz, 2H), 7.10 (d, J = 6.7 Hz, 2H), 4.65 (t, J = 0.9 Hz, 1H), 4.48 (t, J = 11.6 Hz, 1H), 4.00 (dd, J = 10.9, 4.1 Hz, 1H), 1.25 (s, 2H), 0.98 (d, J = 3.6 Hz, 1H), 0.87 (t, J = 2.2 Hz, 2H). | 540.1 |
| 5 | isopropyl-C(=NH)NH | Cl | 29 | (500 MHz, CDCl$_3$): δ 7.87-7.87 (m, 2H), 7.48 (d, J = 8.6 Hz, 2H), 7.40-7.38 (m, 2H), 7.31-7.29 (m, 3H), 7.22-7.20 (m, 2H), 7.10 (dd, J = 2.7, 1.1 Hz, 2H), 5.06 (s, 2H), 4.71 (dd, J = 2.3, 1.3 Hz, 1H), 4.50 (t, J = 11.9 Hz, 1H), 4.08 (d, J = 12.2 Hz, 1H), 2.58 (s, 1H), 1.28 (s, 6H). | 542.1 |
| 6 | 2-iminopiperidinyl | Cl | 29 | (500 MHz, CDCl$_3$): δ 7.87 (d, J = 7.6 Hz, 2H), 7.49 (s, 2H), 7.40 (d, J = 8.1 Hz, 2H), 7.29 (d, J = 7.4 Hz, 3H), 7.20 (d, J = 8.3 Hz, 2H), 7.10-7.08 (m, 2H), 4.70 (s, 1H), 4.55-4.50 (m, 1H), 4.10 (dd, J = 12.5, 4.7 Hz, 1H), 3.41 (s, 2H), 2.46 (s, 2H), 1.77 (dd, J = 20.3, 0.5 Hz, 4H). | 554.1 |
| 7 | adamantyl-C(=NH)NH | Cl | 15 | (500 MHz, CDCl$_3$): δ 7.90 (d, J = 5.8 Hz, 2H), 7.45 (d, J = 8.6 Hz, 2H), 7.39 (d, J = 8.3 Hz, 2H), 7.30-7.26 (m, 3H), 7.20 (d, J = 8.3 Hz, 3H), 7.12 (s, 1H), 4.69 (t, J = 1.6 Hz, 1H), 4.54 (t, J = 11.9 Hz, 1H), 4.04 (dd, J = 12.3, 5.6 Hz, 1H), 2.08 (s, 4H), 1.88 (s, 5H), 1.78-1.69 (m, 5H), 1.62 (t, J = 0.5 Hz, 1H). | 634.2 |
| 8 | phenyl-C(=NH)NH | Cl | 26 | (500 MHz, CDCl$_3$): δ 7.91 (d, J = 7.5 Hz, 2H), 7.77 (d, J = 7.7 Hz, 2H), 7.55 (t, J = 6.9 Hz, 2H), 7.43 (t, J = 7.4 Hz, 5H), 7.38 (d, J = 7.9 Hz, 2H), 7.19 (d, J = 8.0 Hz, 5H), 6.61 (s, 1H), 5.69 (s, 1H), 4.55-4.53 (m, 1H), 4.39-4.38 (m, 1H), 3.97-3.94 (m, 1H). | 576.04 |
| 9 | 4-nitrophenyl-C(=NH)NH | Cl | 62 | — | 621.1 |
| 10 | 4-fluorophenyl-C(=NH)NH | Cl | 7.9 | (500 MHz, CDCl$_3$): δ 7.90 (d, J = 7.7 Hz, 2H), 7.80 (dd, J = 8.6, 5.2 Hz, 2H), 7.43-7.38 (m, 4H), 7.20 (t, J = 7.9 Hz, 3H), 7.10 (t, J = 8.5 Hz, 2H), 6.66 (s, 1H), 5.76 (s, 1H), 4.57 (d, J = 7.0 Hz, 1H), 4.39 (d, J = 3.6 Hz, 1H), 3.96 (s, 1H). | 594.04 |
| 10E1 | 4-fluorophenyl-C(=NH)NH S-enantiomer | Cl | 6.5 | — | 594.04 |
| 10E2 | 4-fluorophenyl-C(=NH)NH R-enantiomer | Cl | 524 | — | 594.04 |

TABLE 2-continued

| Serial # | A | R' | $K_i$ CB$_1$ (nM) | $^1$HNMR | [M + H]$^+$ |
|---|---|---|---|---|---|
| 11 | 4-Cl-C₆H₄-C(=NH)NH₂ | Cl | 10 | (500 MHz, CDCl₃): δ 7.90 (d, J = 7.6 Hz, 2H), 7.72 (d, J = 8.0 Hz, 3H), 7.40-7.38 (m, 6H), 7.20 (t, J = 8.5 Hz, 6H), 6.61 (bs, 1H), 5.95 (s, 1H), 4.57-4.56 (m, 1H), 4.38 (t, J = 12.0 Hz, 1H), 3.93 (d, J = 3.0 Hz, 1H). | 610.9 |
| 11E1 | 4-Cl-C₆H₄-C(=NH)NH₂ (S-enantiomer) | Cl | 15 | — | 610.9 |
| 11E2 | 4-Cl-C₆H₄-C(=NH)NH₂ (R-enantiomer) | Cl | >1000 | — | 610.9 |
| 12 | pyridin-4-yl-C(=NH)NH₂ | Cl | 34 | (500 MHz, CDCl₃): δ 8.72 (s, 2H), 7.86 (d, J = 5.8 Hz, 2H), 7.65 (s, 2H), 7.41-7.38 (m, 6H), 7.20 (t, J = 7.6 Hz, 5H), 6.68 (s, 1H), 6.04 (bs, 1H), 4.60-4.58 (m, 1H), 4.42-4.38 (m, 1H), 3.95-3.93 (m, 1H). | 577.1 |
| 13 | PhO-CH₂-C(=NH)NH₂ | Cl | 72 | (500 MHz, CDCl₃): δ 7.88-7.87 (m, 2H), 7.51 (d, J = 8.1 Hz, 2H), 7.39 (d, J = 8.4 Hz, 2H), 7.34-7.31 (m, 2H), 7.31-7.28 (m, 2H), 7.21 (d, J = 8.6 Hz, 2H), 7.07 (d, J = 15.4 Hz, 2H), 7.04 (t, J = 7.3 Hz, 2H), 6.93 (d, J = 8.0 Hz, 2H), 4.74 (dd, J = 10.1, 1.0 Hz, 3H), 4.54 (t, J = 12.0 Hz, 1H), 4.10 (dd, J = 12.4, 5.2 Hz, 1H). | 606.0 |
| 14 | 3-Br-C₆H₄-C(=NH)NH₂ | Cl | 56 | (500 MHz, CDCl₃): δ 7.87-7.83 (m, 3H), 7.71 (d, J = 7.6 Hz, 1H), 7.65 (d, J = 8.0 Hz, 1H), 7.41 (t, J = 8.7 Hz, 3H), 7.29 (dd, J = 9.8, 6.1 Hz, 2H), 7.23 (s, 4H), 7.18 (d, J = 8.4 Hz, 3H), 6.82 (s, 1H), 5.84 (s, 1H), 4.64-4.62 (m, 1H), 4.47 (t, J = 10.4 Hz, 1H), 3.99 (d, J = 2.9 Hz, 1H). | 655.9 |
| 15 | 2-F-C₆H₄-C(=NH)NH₂ | Cl | 19 | (500 MHz, CDCl₃): δ 7.94-7.90 (m, 3H), 7.52-7.46 (m, 4H), 7.38 (d, J = 7.1 Hz, 3H), 7.21-7.18 (m, 5H), 7.13 (dd, J = 11.2, 8.4 Hz, 2H), 6.73 (s, 1H), 5.87 (s, 1H), 4.61-4.60 (m, 1H), 4.43-4.42 (m, 1H), 4.02-4.01 (m, 1H). | 594.0 |
| 16 | thiophen-2-yl-C(=NH)NH₂ | Cl | 60 | — | 582.1 |
| 17 | 3-MeO-C₆H₄-C(=NH)NH₂ | Cl | 86 | (500 MHz, CDCl₃): δ 7.91 (d, J = 7.9 Hz, 2H), 7.38 (d, J = 8.4 Hz, 4H), 7.33-7.29 (m, 4H), 7.18 (d, J = 8.4 Hz, 5H), 7.06 (s, 2H), 6.61 (s, 1H), 5.87 (s, 1H), 4.52 (s, 1H), 4.37 (s, 1H), 3.95 (s, 1H), 3.75 (s, 3H). | 606.0 |

TABLE 2-continued

| Serial # | A | R' | K$_i$ CB$_1$ (nM) | $^1$HNMR | [M + H]$^+$ |
|---|---|---|---|---|---|
| 18 | pyridine-2-carboxamidine | Cl | 26 | (500 MHz, CDCl$_3$): δ 8.97 (s, 1H), 8.65 (d, J = 4.1 Hz, 2H), 8.34 (d, J = 7.8 Hz, 2H), 7.86 (d, J = 7.7 Hz, 3H), 7.51 (d, J = 5.7 Hz, 2H), 7.32 (t, J = 7.0 Hz, 3H), 7.16 (s, 4H), 4.73 (s, 1H), 4.64 (s, 1H), 4.20 (s, 1H). | 577.0 |
| 19 | 2,4-difluorobenzamidine | Cl | 7.7 | (500 MHz, CDCl$_3$): δ 7.87 (d, J = 6.9 Hz, 2H), 7.45-7.44 (m, 2H), 7.37 (d, J = 7.6 Hz, 2H), 7.20 (d, J = 13.2 Hz, 8H), 6.94 (t, J = 7.3 Hz, 1H), 6.87 (d, J = 10.8 Hz, 1H), 6.76 (s, 1H), 6.21 (s, 1H), 4.63 (d, J = 6.3 Hz, 1H), 4.48 (d, J = 8.5 Hz, 1H), 3.98-3.96 (m, 1H). | 612.08 |
| 20 | 4-bromobenzamidine | Cl | 27 | (500 MHz, CDCl$_3$): δ 7.90-7.89 (m, 2H), 7.65 (d, J = 8.1 Hz, 3H), 7.56 (d, J = 8.0 Hz, 3H), 7.40 (s, 5H), 7.20 (d, J = 8.4 Hz, 3H), 6.63 (s, 1H), 5.77 (s, 1H), 4.55 (s, 1H), 4.37 (s, 1H), 3.94 (s, 1H). | 655.9 |
| 21 | S-methylisothiourea | Cl | 67 | (500 MHz, CDCl$_3$): δ 7.88 (d, J = 6.3 Hz, 2H), 7.46 (d, J = 8.4 Hz, 2H), 7.39 (d, J = 8.4 Hz, 2H), 7.27 (t, J = 12.4 Hz, 3H), 7.19 (d, J = 8.5 Hz, 2H), 7.13 (s, 2H), 4.70 (t, J = 0.6 Hz, 1H), 4.55 (t, J = 11.8 Hz, 1H), 4.05 (dd, J = 12.2, 5.3 Hz, 1H), 2.28 (s, 3H). | 546.1 |
| 22 | S-ethylisothiourea | Cl | 67 | (500 MHz, CDCl$_3$): δ 7.90-7.88 (m, 2H), 7.48 (d, J = 8.5 Hz, 2H), 7.40 (d, J = 8.3 Hz, 2H), 7.30 (d, J = 7.4 Hz, 2H), 7.26 (d, J = 7.0 Hz, 1H), 7.21 (d, J = 8.5 Hz, 2H), 7.14 (t, J = 0.5 Hz, 2H), 4.70 (d, J = 10.3 Hz, 1H), 4.54 (t, J = 11.8 Hz, 1H), 4.09 (dd, J = 12.2, 5.1 Hz, 1H), 2.83 (s, 2H), 1.31 (t, J = 7.1 Hz, 4H). | 560.07 |
| 23 | S-isopropylisothiourea | Cl | 166 | (500 MHz, CDCl$_3$): δ 7.90-7.89 (m, 2H), 7.48 (d, J = 7.6 Hz, 2H), 7.41 (d, J = 7.6 Hz, 2H), 7.31 (d, J = 6.8 Hz, 2H), 7.21 (d, J = 7.7 Hz, 2H), 7.12 (s, 3H), 5.12 (bs, 1H), 4.70-4.68 (m, 1H), 4.52-4.50 (m, 1H), 4.13-4.09 (m, 1H), 3.23 (m, 1H), (1.37-1.33 (m, 6H). | 574.0 |
| 24 | S-benzylisothiourea | Cl | 127 | (500 MHz, CDCl$_3$): δ 7.88 (t, J = 1.1 Hz, 2H), 7.38 (d, J = 8.1 Hz, 4H), 7.31 (s, 5H), 7.17 (d, J = 8.4 Hz, 4H), 7.10 (s, 3H), 4.71 (s, 1H), 4.57-4.55 (m, 1H), 4.06-3.99 (m, 3H). | 622.08 |
| 25 | S-phenethylisothiourea | Cl | 287 | (500 MHz, CDCl$_3$): δ 7.89 (d, J = 1.6 Hz, 2H), 7.47 (d, J = 7.8 Hz, 2H), 7.37 (d, J = 6.9 Hz, 2H), 7.30 (d, J = 6.8 Hz, 3H), 7.23-7.22 (m, 3H), 7.18 (d, J = 8.1 Hz, 3H), 7.11 (s, 3H), 4.70 (s, 1H), 4.54 (t, J = 11.6 Hz, 1H), 4.11-4.08 (m, 1H), 3.03 (s, 2H), 2.97 (s, 2H). | 636.1 |
| 26 | S-(3-phenylpropyl)isothiourea | Cl | 190 | (500 MHz, CDCl$_3$): δ 7.86 (s, 2H), 7.39 (d, J = 18.6 Hz, 3H), 7.29 (s, 3H), 7.20 (d, J = 6.6 Hz, 2H), 7.17 (d, J = 6.4 Hz, 2H), 7.10 (s, 6H), 4.71 (s, 1H), 4.56-4.51 (m, 1H), 4.06 (s, 1H), 2.72 (s, 1H), 2.64 (d, J = 5.9 Hz, 2H), 1.97 (s, 3H). | 650.1 |
| 27 | acetamidine | F | 60 | (500 MHz, CDCl$_3$): δ 7.95-7.93 (m, 2H), 7.51 (d, J = 8.0 Hz, 2H), 7.29 (d, J = 7.0 Hz, 2H), 7.21 (d, J = 8.3 Hz, 3H), 7.09 (t, J = 7.3 Hz, 4H), 5.29 (bs, 2H), 4.71 (dd, J = 11.4, 4.9 Hz, 1H), 4.49 (t, J = 11.9 Hz, 1H), 4.11-4.09 (m, 1H), 2.08 (s, 3H). | 498.1 |

US 11,485,709 B2

TABLE 2-continued

| Serial # | A | R' | $K_i$ CB$_1$ (nM) | $^1$HNMR | [M + H]$^+$ |
|---|---|---|---|---|---|
| 28 | 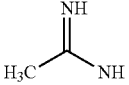 | Br | 18 | (500 MHz, CDCl$_3$): δ 7.80 (d, J = 7.5 Hz, 2H), 7.55 (d, J = 8.3 Hz, 2H), 7.51 (d, J = 8.5 Hz, 2H), 7.30 (d, J = 7.6 Hz, 3H), 7.22 (d, J = 8.5 Hz, 2H), 7.09-7.08 (m, 2H), 5.11 (bs, 2H), 4.71 (dt, J = 6.3, 0.9 Hz, 1H), 4.49 (t, J = 12.0 Hz, 1H), 4.11 (t, J = 6.7 Hz, 1H), 2.08 (s, 3H). | 558.03 |
| 29 | 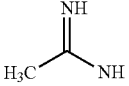 | I | 10 | 500 MHz, CDCl$_3$): δ 7.77 (d, J = 8.0 Hz, 2H), 7.67-7.64 (m, 2H), 7.51 (d, J = 7.7 Hz, 2H), 7.30 (s, 3H), 7.23-7.21 (m, 2H), 7.09-7.08 (m, 2H), 5.14 (s, 1H), 4.71 (d, J = 8.0 Hz, 1H), 4.51-4.46 (m, 1H), 4.10 (d, J = 10.6 Hz, 1H), 2.08 (s, 3H). | 606.1 |
| 30 | 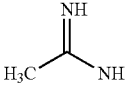 | H | 114 | (500 MHz, CDCl$_3$): δ 7.94 (d, J = 7.1 Hz, 2H), 7.50 (d, J = 8.3 Hz, 2H), 7.46 (d, J = 6.7 Hz, 2H), 7.42 (t, J = 7.2 Hz, 2H), 7.30 (t, J = 7.1 Hz, 2H), 7.21 (d, J = 8.4 Hz, 2H), 7.09-7.08 (m, 2H), 5.19 (bs, 1H), 4.72-4.69 (m, 1H), 4.50 (t, J = 12.0 Hz, 1H), 4.13-4.10 (m, 1H), 2.05 (s, 3H). | 480.1 |
| 31 | 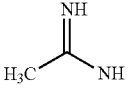 | CH$_3$ | 87 | (500 MHz, CDCl$_3$): δ 7.81 (d, J = 7.8 Hz, 2H), 7.47 (d, J = 8.5 Hz, 2H), 7.25-7.22 (m, 3H), 7.18 (dd, J = 12.0, 8.4 Hz, 4H), 7.06 (d, J = 7.0 Hz, 2H), 5.82 (s, 1H), 4.68 (dd, J = 11.2, 4.8 Hz, 1H), 4.49 (t, J = 11.3 Hz, 1H), 4.06 (t, J = 6.6 Hz, 1H), 2.35 (s, 3H), 2.00 (s, 3H). | 494.1 |
| 32 | 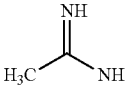 | OCH$_3$ | 182 | (500 MHz, CDCl$_3$): δ 7.86 (d, J = 7.8 Hz, 2H), 7.49 (d, J = 7.4 Hz, 2H), 7.27 (d, J = 6.5 Hz, 3H), 7.20-7.18 (m, 2H), 7.07 (d, J = 6.7 Hz, 2H), 6.90-6.88 (m, 2H), 4.70-4.67 (m, 1H), 4.51-4.46 (m, 1H), 4.07 (s, 1H), 3.82 (s, 3H), 2.03 (s, 3H). | 510.1 |
| 33 | 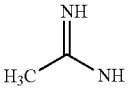 | —(C$_4$H$_8$)— | 8 | (500 MHz, CDCl$_3$): δ 8.48 (s, 1H), 7.96 (d, J = 8.4 Hz, 1H), 7.92-7.91 (m, 1H), 7.87 (t, J = 7.4 Hz, 2H), 7.58-7.52 (m, 2H), 7.48 (d, J = 8.4 Hz, 3H), 7.28 (s, 2H), 7.18 (d, J = 7.7 Hz, 2H), 7.08 (d, J = 6.9 Hz, 2H), 5.22 (s, 1H), 4.70-4.69 (m, 1H), 4.51 (t, J = 12.0 Hz, 1H), 4.14-4.11 (m, 1H), 2.04 (s, 3H). | 530.1 |
| 34 | 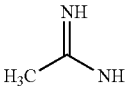 | CF$_3$ | 5.7 | (500 MHz, CDCl$_3$): δ 8.05 (d, J = 5.7 Hz, 2H), 7.69-7.68 (m, 2H), 7.50 (d, J = 8.0 Hz, 2H), 7.29 (d, J = 7.2 Hz, 2H), 7.21 (d, J = 8.0 Hz, 3H), 7.09-7.08 (m, 2H), 4.73-4.71 (m, 1H), 4.51 (t, J = 11.5 Hz, 1H), 3.87 (d, J = 5.1 Hz, 1H), 2.09 (s, 3H). | 548.1 |
| 35 | 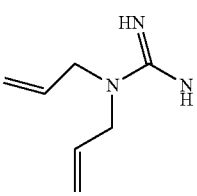 | Cl | 263 | (500 MHz, CDCl$_3$): δ 7.93 (d, J = 8.4 Hz, 2H), 7.40 (d, J = 8.4 Hz, 2H), 7.31 (t, J = 7.5 Hz, 2H), 7.24 (s, 3H), 7.18 (d, J = 7.4 Hz, 2H), 7.14 (d, J = 8.5 Hz, 2H), 5.76 (td, J = 11.1, 5.6 Hz, 2H), 5.23-5.20 (m, 4H), 4.56 (dd, J = 11.3, 4.6 Hz, 1H), 4.48 (t, J = 11.5 Hz, 1H), 4.04 (dd, J = 11.8, 4.6 Hz, 1H), 3.98-3.89 (m, 4H). | 595.1 |
| 36 | 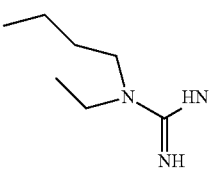 | Cl | 535 | (500 MHz, CDCl$_3$): δ 7.94 (d, J = 8.3 Hz, 2H), 7.40 (d, J = 8.4 Hz, 2H), 7.31-7.29 (m, 3H), 7.19 (d, J = 0.9 Hz, 3H), 7.13 (d, J = 8.5 Hz, 3H), 4.56-4.53 (m, 1H), 4.50-4.47 (m, 1H), 4.05-4.02 (m, 1H), 3.40-3.29 (m, 2H), 3.38-3.29 (m, 2H), 1.84 (m, 4H), 0.91 (s, 3H), 0.88 (s, 3H). | 599.1 |

TABLE 2-continued

| Serial # | A | R' | K_i CB_1 (nM) | 1HNMR | [M + H]+ |
|---|---|---|---|---|---|
| 37 | (dipropyl guanidine) | Cl | 138 | (500 MHz, CDCl_3): δ 7.95-7.93 (m, 2H), 7.41-7.39 (m, 2H), 7.30 (dd, J = 5.0, 1.9 Hz, 3H), 7.20-7.18 (m, 4H), 7.13 (d, J = 6.8 Hz, 2H), 4.54 (d, J = 11.5 Hz, 1H), 4.47 (t, J = 11.5 Hz, 1H), 4.05-4.02 (m, 1H), 3.30 (m, 2H), 3.18 (m, 2H), 1.30-1.28 (m, 2H), 1.17 (d, J = 24.7 Hz, 2H), 0.89-0.88 (m, 6H). | 599.1 |
| 38 | (diethyl guanidine) | Cl | 49 | (500 MHz, CDCl_3): δ 7.93 (d, J = 8.3 Hz, 2H), 7.40-7.38 (m, 2H), 7.29 (d, J = 7.4 Hz, 2H), 7.24-7.23 (m, 2H), 7.17 (d, J = 7.8 Hz, 2H), 7.11 (d, J = 8.2 Hz, 3H), 4.55-4.52 (m, 1H), 4.46 (t, J = 11.4 Hz, 1H), 4.03-4.00 (m, 1H), 3.30-3.27 (m, 2H), 3.20-3.16 (m, 2H), 0.86 (t, J = 5.7 Hz, 6H). | 571.1 |
| 39 | (bis(methoxyethyl) guanidine) | Cl | 425 | (500 MHz, CDCl_3): δ 7.93 (d, J = 8.5 Hz, 2H), 7.39 (d, J = 8.5 Hz, 2H), 7.30 (d, J = 7.3 Hz, 4H), 7.25 (q, J = 8.4 Hz, 2H), 7.15 (dd, J = 11.0, 8.4 Hz, 3H), 4.56 (dd, J = 11.2, 4.7 Hz, 1H), 4.45 (t, J = 11.6 Hz, 1H), 4.04-4.01 (m, 1H), 3.54 (d, J = 3.5 Hz, 8H), 3.30 (s, 6H). | 631.1 |
| 40 | (methoxyethyl guanidine) | Cl | 848 | (500 MHz, CDCl_3): δ 7.93 (d, J = 8.4 Hz, 2H), 7.40 (d, J = 8.4 Hz, 2H), 7.29 (t, J = 7.4 Hz, 3H), 7.24 (d, J = 7.2 Hz, 1H), 7.18 (d, J = 0.6 Hz, 2H), 7.13 (t, J = 8.0 Hz, 3H), 4.55 (dd, J = 11.3, 4.5 Hz, 1H), 4.44 (t, J = 11.7 Hz, 1H), 4.03 (dd, J = 12.0, 4.6 Hz, 1H), 3.44 (d, J = 4.4 Hz, 2H), 3.34 (d, J = 7.8 Hz, 2H), 3.31 (s, 3H). | 573.1 |
| 41 | (BocHN guanidine) | Cl | 6.5 | (500 MHz, CDCl_3): δ 8.02 (d, J = 8.4 Hz, 2H), 7.60 (d, J = 8.6 Hz, 2H), 7.49 (d, J = 8.5 Hz, 2H), 7.38 (d, J = 7.6 Hz, 3H), 7.34-7.31 (m, 2H), 7.26 (dd, J = 14.0, 8.0 Hz, 2H), 4.71 (dd, J = 11.2, 4.9 Hz, 1H), 4.55 (t, J = 11.7 Hz, 1H), 4.16 (dd, J = 12.2, 4.9 Hz, 1H), 1.54 (s, 9H). | 615.07 |
| 42 | (N-methoxy-N-methyl guanidine) | Cl | 23 | (500 MHz, CDCl_3): δ 7.93 (d, J = 8.4 Hz, 2H), 7.40 (d, J = 8.4 Hz, 2H), 7.31 (t, J = 7.5 Hz, 2H), 7.24 (s, 2H), 7.18 (d, J = 7.4 Hz, 3H), 7.14 (d, J = 8.5 Hz, 2H), 4.56 (dd, J = 11.3, 4.6 Hz, 1H), 4.48 (t, J = 11.5 Hz, 1H), 4.04 (dd, J = 11.8, 4.6 Hz, 1H), 3.59 (s, 3H), 3.02 (s, 3H). | 559.4 |
| 43 | (N-(2-methoxyethyl)-N-methyl guanidine) | Cl | 908 | (500 MHz, CDCl_3): δ 7.95-7.93 (m, 2H), 7.39 (d, J = 8.1 Hz, 2H), 7.31-7.29 (m, 3H), 7.18-7.14 (m, 6H), 4.56-4.54 (m, 1H), 4.49-4.45 (m, 1H), 4.05 (d, J = 7.2 Hz, 1H), 3.54 (s, 2H), 3.49-3.47 (m, 2H), 3.34 (s, 3H), 3.00 (s, 3H). | 587.1 |
| 44 | (N,N-dimethyl guanidine) | Cl | 171 | (500 MHz, CDCl_3): δ 7.92 (d, J = 8.4 Hz, 2H), 7.40 (d, J = 8.4 Hz, 2H), 7.29 (t, J = 7.4 Hz, 2H), 7.23 (d, J = 7.2 Hz, 1H), 7.15 (d, J = 7.3 Hz, 3H), 7.10 (s, 4H), 4.53 (dd, J = 11.3, 4.5 Hz, 1H), 4.46 (t, J = 11.5 Hz, 1H), 4.02 (dd, J = 11.7, 4.5 Hz, 1H), 2.98 (s, 6H). | 543.1 |
| 45 | (N-methyl guanidine) | Cl | 327 | (500 MHz, CDCl_3): δ 7.90 (d, J = 8.3 Hz, 2H), 7.40 (d, J = 8.5 Hz, 2H), 7.29 (d, J = 7.0 Hz, 2H), 7.23 (d, J = 7.3 Hz, 1H), 7.13-7.09 (m, 6H), 4.54 (dd, J = 11.2, 4.6 Hz, 1H), 4.44 (t, J = 11.7 Hz, 1H), 4.01 (dd, J = 11.9, 4.6 Hz, 1H), 2.73 (d, J = 2.4 Hz, 3H). | 529.1 |

TABLE 2-continued

| Serial # | A | R' | $K_i$ CB$_1$ (nM) | $^1$HNMR | [M + H]$^+$ |
|---|---|---|---|---|---|
| 46 | *tert*-butyl guanidine | Cl | 49 | (500 MHz, CDCl$_3$): δ 7.92 (d, J = 8.2 Hz, 2H), 7.41 (d, J = 8.1 Hz, 2H), 7.30 (t, J = 7.2 Hz, 3H), 7.14 (d, J = 7.4 Hz, 3H), 7.10 (s, 3H), 4.54 (t, J = 5.5 Hz, 1H), 4.49 (t, J = 11.3 Hz, 1H), 4.05-4.02 (m, 1H), 1.30 (s, 9H). | 571.1 |
| 47 | isopropyl guanidine | Cl | 516 | (500 MHz, CDCl$_3$): δ 7.92 (d, J = 8.4 Hz, 2H), 7.41 (d, J = 8.4 Hz, 2H), 7.31-7.22 (m, 3H), 7.14 (d, J = 7.3 Hz, 3H), 7.10 (d, J = 7.2 Hz, 3H), 4.54 (dd, J = 11.2, 4.5 Hz, 1H), 4.45 (t, J = 11.6 Hz, 1H), 4.03 (dd, J = 11.9, 4.6 Hz, 1H), 3.82 (s, 1H), 1.11 (dd, J = 9.8, 6.6 Hz, 6H). | 557.0 |
| 48 | pyridin-3-ylmethyl N-methyl guanidine | Cl | 147 | (500 MHz, CDCl$_3$): δ 8.54-8.51 (m, 3H), 7.89 (d, J = 8.4 Hz, 2H), 7.67 (s, 1H), 7.38-7.32 (m, 3H), 7.23 (d, J = 8.6 Hz, 5H), 7.10 (d, J = 25.6 Hz, 3H), 4.67-4.66 (m, 3H), 4.44 (s, 1H), 4.10 (d, J = 8.4 Hz, 1H), 3.10 (s, 3H). | 620.1 |
| 49 | N-benzyl-N-methyl guanidine | Cl | 343 | (500 MHz, CDCl$_3$): δ 7.93-7.91 (m, 2H), 7.36 (d, J = 7.0 Hz, 2H), 7.27 (d, J = 11.6 Hz, 7H), 7.20 (d, J = 7.7 Hz, 4H), 7.13 (t, J = 8.1 Hz, 3H), 4.74 (d, J = 15.2 Hz, 1H), 4.51 (d, J = 11.5 Hz, 1H), 4.45 (dd, J = 20.1, 7.6 Hz, 2H), 4.01-3.98 (m, 1H), 2.94 (s, 3H). | 619.1 |
| 50 | N,N'-dibenzyl guanidine | Cl | 505 | (500 MHz, CDCl$_3$): 7.81 (d, J = 8.3 Hz, 2H), 7.32-7.22 (m, 14H), 7.09 (d, J = 7.1 Hz, 2H), 4.51-4.28 (m, 4H), 3.97-3.94 (m, 1H) | 605.1 |
| 51 | phenethyl guanidine | Cl | 931 | (500 MHz, CDCl$_3$): δ 7.89 (d, J = 7.7 Hz, 2H), 7.40 (d, J = 7.5 Hz, 2H), 7.29 (d, J = 6.9 Hz, 2H), 7.20 (d, J = 6.3 Hz, 5H), 7.14-7.07 (m, 7H), 4.55-4.53 (m, 1H), 4.43 (t, J = 11.4 Hz, 1H), 4.03-4.00 (m, 1H), 3.41-3.39 (m, 2H), 2.77 (d, J = 6.8 Hz, 2H). | 619.1 |
| 52 | morpholine carboxamidine | Cl | 193 | (500 MHz, CDCl$_3$): δ 7.90 (d, J = 8.5 Hz, 2H), 7.41 (d, J = 8.5 Hz, 2H), 7.30 (t, J = 7.4 Hz, 2H), 7.23 (t, J = 7.4 Hz, 2H), 7.14-7.07 (m, 7H), 4.53 (dd, J = 11.2, 4.6 Hz, 1H), 4.45 (t, J = 11.5 Hz, 1H), 4.01 (dd, J = 11.7, 4.6 Hz, 1H), 3.66 (t, J = 4.5 Hz, 4H), 3.51 (d, J = 4.4 Hz, 4H). | 585.1 |
| 53 | piperidine carboxamidine | Cl | 276 | (500 MHz, CDCl$_3$): δ 7.92 (d, J = 8.2 Hz, 2H), 7.38 (d, J = 8.2 Hz, 2H), 7.29-7.26 (m, 4H), 7.22 (t, J = 7.3 Hz, 2H), 7.13 (t, J = 9.5 Hz, 3H), 4.54 (t, J = 5.6 Hz, 1H), 4.47 (t, J = 11.5 Hz, 1H), 4.02 (dd, J = 11.7, 4.6 Hz, 1H), 3.43 (s, 4H), 1.62 (d, J = 4.3 Hz, 2H), 1.55 (s, 4H). | 583.1 |
| 54 | 4-methylpiperazine carboxamidine | Cl | 309 | (500 MHz, CDCl$_3$): δ 7.91 (d, J = 8.2 Hz, 2H), 7.40 (d, J = 8.2 Hz, 2H), 7.30 (t, J = 7.4 Hz, 3H), 7.25 (s, 1H), 7.14 (dd, J = 13.8, 8.2 Hz, 5H), 4.55 (dd, J = 11.2, 4.7 Hz, 1H), 4.47 (t, J = 11.5 Hz, 1H), 4.02 (dd, J = 11.7, 4.7 Hz, 1H), 3.51 (s, 4H), 2.39 (s, 4H), 2.30 (s, 3H). | 598.1 |

TABLE 2-continued

| Serial # | A | R' | $K_i$ CB$_1$ (nM) | $^1$HNMR | [M + H]$^+$ |
|---|---|---|---|---|---|
| 55 | pyrrolidine carboxamidine | Cl | 241 | (500 MHz, CDCl$_3$): δ 7.93 (d, J = 8.2 Hz, 2H), 7.39 (d, J = 7.8 Hz, 2H), 7.28-7.22 (d, J = 7.0 Hz, 3H), 7.15 (d, J = 7.5 Hz, 2H), 7.09 (s, 4H), 4.52 (dd, J = 11.2, 4.5 Hz, 1H), 4.44 (t, J = 11.6 Hz, 1H), 4.01 (dd, J = 11.9, 4.5 Hz, 1H), 3.36 (m, 4H), 1.89 (m, 4H). | 569.1 |
| 56 | cyclopentyl guanidine | Cl | 459 | (500 MHz, CDCl$_3$): δ 7.94 (d, J = 8.5 Hz, 2H), 7.41 (d, J = 8.5 Hz, 2H), 7.29 (d, J = 7.6 Hz, 3H), 7.23 (s, 1H), 7.16 (d, J = 7.3 Hz, 3H), 7.13 (d, J = 8.3 Hz, 2H), 4.56-4.53 (m, 1H), 4.45 (t, J = 11.5 Hz, 1H), 4.06-4.03 (m, 1H), 3.78 (m, 1H), 1.88-1.86 (m, 2H), 1.63 (s, 2H), 1.53 (dd, J = 4.3, 1.1 Hz, 2H), 1.41-1.38 (m, 2H). | 583.1 |
| 57 | cyclohexyl guanidine | Cl | 419 | (500 MHz, CDCl$_3$): δ 7.93 (d, J = 8.3 Hz, 2H), 7.41 (d, J = 8.3 Hz, 2H), 7.30 (t, J = 7.2 Hz, 3H), 7.23 (d, J = 7.0 Hz, 1H), 7.15 (d, J = 7.5 Hz, 3H), 7.13-7.11 (m, 2H), 4.56-4.53 (m, 1H), 4.44 (t, J = 11.5 Hz, 1H), 4.05-4.02 (m, 1H), 3.45 (m, 1H), 1.85-1.83 (m, 2H), 1.66-1.65 (m, 2H), 1.58 (m, 4H), 1.13-1.11 (m, 2H). | 597.1 |
| 58 | tryptamine guanidine | Cl | 585 | (500 MHz, CDCl$_3$): δ 8.10 (s, 1H), 7.84 (d, J = 7.9 Hz, 2H), 7.49 (d, J = 7.7 Hz, 1H), 7.30 (dt, J = 13.2, 8.0 Hz, 7H), 7.18-7.14 (m, 2H), 7.14-7.11 (m, 3H), 7.04 (d, J = 9.2 Hz, 2H), 4.49-4.47 (m, 1H), 4.36-4.32 (m, 1H), 3.99-3.96 (m, 1H), 3.46-3.42 (m, 2H), 2.94-2.91 (m, 2H). | 658.1 |
| 59 | Boc-piperazine carboxamidine | Cl | 387 | (500 MHz, CDCl$_3$): δ 7.92 (d, J = 8.3 Hz, 2H), 7.41 (s, 2H), 7.30 (d, J = 7.3 Hz, 3H), 7.16 (t, J = 8.3 Hz, 6H), 4.59-4.56 (m, 1H), 4.49-4.44 (m, 1H), 4.03 (dd, J = 11.9, 4.7 Hz, 1H), 3.49-3.48 (m, 8H), 1.46 (s, 9H). | 684.1 |
| 60 | 1,3-dimethoxypropyl guanidine | Cl | 443 | 500 MHz, CDCl$_3$): δ 7.92 (d, J = 7.3 Hz, 2H), 7.41-7.40 (m, 2H), 7.31-7.28 (m, 3H), 7.24 (s, 2H), 7.14 (d, J = 4.6 Hz, 4H), 4.57-4.55 (m, 1H), 4.45 (t, J = 11.6 Hz, 1H), 4.40 (s, 1H), 4.04 (dd, J = 11.5, 4.0 Hz, 1H), 3.37 (d, J = 6.5 Hz, 2H), 3.32 (s, 6H). | 603.1 |
| 61 | N-methyl-N-cyanoethyl guanidine | Cl | 203 | (500 MHz, CDCl$_3$): δ 7.90 (d, J = 8.3 Hz, 2H), 7.41 (d, J = 8.4 Hz, 2H), 7.30 (d, J = 7.4 Hz, 2H), 7.16 (d, J = 17.8 Hz, 3H), 7.14 (d, J = 7.7 Hz, 4H), 4.58 (dd, J = 10.9, 4.5 Hz, 1H), 4.47 (t, J = 11.5 Hz, 1H), 4.35 (m, 1H), 3.99 (dd, J = 11.8, 4.8 Hz, 1H), 3.5 (m, 1H), 3.13 (s, 3H), 2.66 (d, J = 5.7 Hz, 2H). | 582.1 |
| 62 | adamantylmethyl guanidine | Cl | >1000 | (500 MHz, CDCl$_3$): δ 7.93 (d, J = 8.5 Hz, 2H), 7.41 (d, J = 8.4 Hz, 2H), 7.30-7.28 (m, 4H), 7.16 (d, J = 7.1 Hz, 2H), 7.12 (d, J = 7.1 Hz, 3H), 4.56-4.52 (m, 1H), 4.47-4.42 (m, 1H), 4.07-4.04 (m, 1H), 2.83-2.75 (m, 1H), 2.74 (d, J = 8.9 Hz, 1H), 1.95 (s, 4H), 1.70-1.68 (m, 5H), 1.60 (s, 3H), 1.30-1.25 (m, 3H). | 663.2 |
| 63 | pyrazolyl carboxamidine | Cl | 11 | (500 MHz, CDCl$_3$): δ 7.91 (s, 2H), 7.68 (s, 1H), 7.47-7.43 (m, 4H), 7.40-7.30 (m, 4H), 7.17 (s, 5H), 6.43 (s, 1H), 4.75 (s, 2H), 4.14 (d, J = 16.7 Hz, 1H). | 566.0 |

TABLE 2-continued

| Serial # | A | R' | K$_i$ CB$_1$ (nM) | $^1$HNMR | [M + H]$^+$ |
|---|---|---|---|---|---|
| 64 | (adamantyl guanidine) | Cl | >1000 | (500 MHz, CDCl$_3$): δ 7.94 (d, J = 7.8 Hz, 2H), 7.41 (d, J = 7.9 Hz, 2H), 7.32-7.28 (m, 4H), 7.16 (dd, J = 14.3, 7.8 Hz, 5H), 4.58-4.55 (m, 1H), 4.49-4.45 (m, 1H), 4.09-4.05 (m, 1H), 2.04 (s, 6H), 1.83 (m, 5H), 1.66-1.64 (m, 4H). | 649.2 |
| 65 | (acetyl guanidine) | Cl | 9 | (500 MHz, CDCl$_3$): δ 7.92 (d, J = 7.2 Hz, 2H), 7.47 (d, J = 7.9 Hz, 2H), 7.38 (d, J = 7.6 Hz, 2H), 7.30 (d, J = 21.1 Hz, 3H), 7.19 (d, J = 8.1 Hz, 2H), 7.11-7.10 (m, 2H), 4.56-4.50 (m, 2H), 4.04-4.01 (m, 1H), 1.86 (s, 3H). | 557.0 |
| 66 | (cumyl guanidine) | Cl | 112 | (500 MHz, CDCl$_3$): δ 7.96 (d, J = 7.5 Hz, 2H), 7.40 (t, J = 9.3 Hz, 7H), 7.30-7.29 (m, 4H), 7.15 (d, J = 7.8 Hz, 5H), 4.52 (s, 2H), 4.40-4.34 (m, 1H), 4.01-3.98 (m, 1H), 1.51 (s, 11H). | 633.2 |
| 67 | (N-methyl-N-neopentyl guanidine) | Cl | 2390 | (500 MHz, CDCl$_3$): δ 7.94 (d, J = 8.4 Hz, 2H), 7.40 (d, J = 8.4 Hz, 2H), 7.33-7.30 (m, 3H), 7.19 (d, J = 7.2 Hz, 3H), 7.14 (d, J = 8.5 Hz, 3H), 4.57-4.54 (m, 1H), 4.48 (t, J = 11.4 Hz, 1H), 4.07-4.04 (m, 1H), 3.10 (s, 1H), 3.07 (s, 1H), 3.02 (s, 3H), 0.97-0.94 (m, 9H). | 599.2 |
| 68 | (dimethoxy-methyl guanidine) | Cl | 443 | (500 MHz, CDCl$_3$): δ 7.94 (d, J = 8.2 Hz, 2H), 7.40 (d, J = 8.3 Hz, 2H), 7.30-7.28 (m, 5H), 7.18-7.14 (m, 4H), 4.58-4.55 (m, 1H), 4.49-4.46 (m, 2H), 4.06-4.04 (m, 1H), 3.47 (s, 1H), 3.40 (s, 6H), 3.02 (s, 3H). | 617.1 |
| 69 | (dimethylpyrazolyl amidine) | Cl | 10 | (500 MHz, CDCl$_3$): δ 7.91 (dd, J = 1.5, 0.5 Hz, 2H), 7.51-7.50 (m, 2H), 7.39 (s, 2H), 7.35-7.29 (m, 4H), 7.20 (d, J = 8.0 Hz, 3H), 5.99 (s, 1H), 4.71-4.69 (m, 1H), 4.56 (t, J = 11.5 Hz, 1H), 4.12 (dd, J = 11.8, 4.4 Hz, 1H), 2.43 (s, 3H), 2.23 (s, 3H). | 594.1 |
| 70 | (acetyl guanidine) | I | 3.2 | (500 MHz, CDCl$_3$): δ 7.80 (d, J = 8.1 Hz, 2H), 7.73 (d, J = 8.0 Hz, 2H), 7.43 (d, J = 8.3 Hz, 2H), 7.33 (t, J = 7.3 Hz, 2H), 7.28 (s, 1H), 7.20 (d, J = 8.5 Hz, 2H), 7.15 (d, J = 7.0 Hz, 2H), 4.61-4.59 (m, 1H), 4.49 (t, J = 11.6 Hz, 1H), 4.07 (dd, J = 12.9, 4.9 Hz, 1H), 1.95 (s, 3H). | 637.0 |
| 71 | (acetyl guanidine) | —(C4H8)— | 16 | (400 MHz, CDCl$_3$): δ 8.54 (s, 1H), 8.04 (d, J = 8.0 Hz, 1H), 7.92-7.89 (m, 3H), 7.42 (d, 2H), 7.48 (d, J = 8.4 Hz, 2H), 7.29 (m, 3H), 7.15 (d, J = 7.7 Hz, 2H), 7.05 (d, J = 6.9 Hz, 2H), 4.59-4.57 (m, 1H), 4.51 (t, J = 12.0 Hz, 1H), 4.04-3.99 (m, 1H), 1.78 (s, 3H). | 562.1 |

TABLE 2-continued

| Serial # | A | R' | K$_i$ CB$_1$ (nM) | $^1$HNMR | [M + H]$^+$ |
|---|---|---|---|---|---|
| 72 | O=C(CH$_3$)-NH-C(=NH)-NH | CF3 | 2.7 | (400 MHz, CDCl$_3$): δ 8.14 (d, J = 8.0 Hz, 2H), 7.73 (d, J = 8.0 Hz, 2H), 7. 38 (d, J = 8.3 Hz, 2H), 7.33 (m, 3H), 7.15 (d, J = 8.0 Hz, 4H), 4.63 (dd, J = 12, 5.0 Hz, 1H), 4.50 (t, J = 12.0 Hz, 1H), 4.09 (dd, J = 11.8, 4.8 Hz, 1H), 1.94 (s, 3H). | 580.0 |
| 73 | NH$_2$NH | Cl | 33 | — | 488.1 |

Figure 5A:
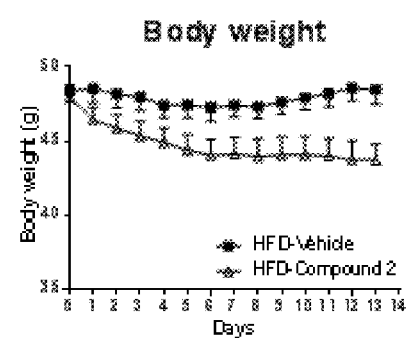
Figure 5B:
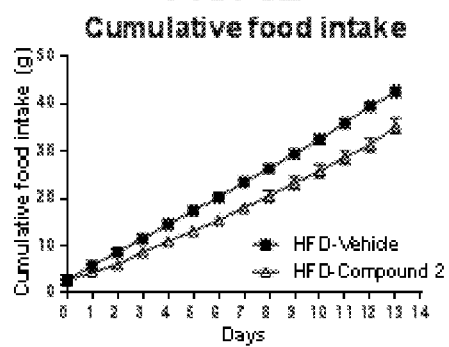
Figure 5C:
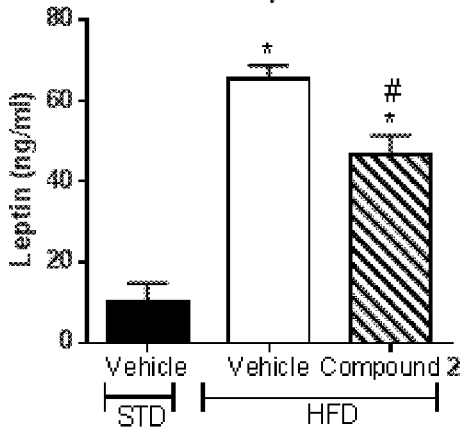
Figure 5D:
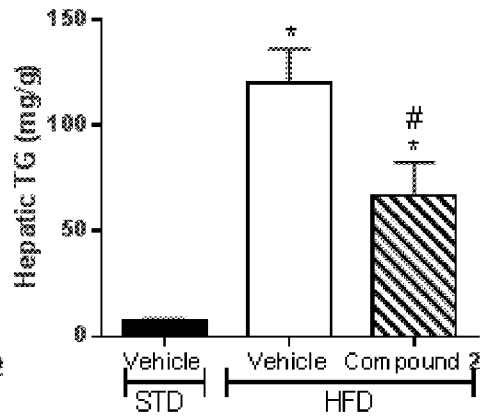

Using radioligand displacement assay in mouse brain membranes, the Ki of one of the enantiomers of compound 2 (compound 2E1) is 9 nM. Measuring its tissue levels 1 hour after administration of 10 mg/kg to mice, plasma levels were comparable after oral or i.p. administration (indicating good oral bioavailability), and brain tissue level was <2% of plasma level, indicating low brain penetrance/peripheral selectivity. 1 h after oral administration of compound 2 at 10 mg/kg dose in mice, the metabolite generation in plasma was monitored by LC-MS/MS. As expected, this compound underwent in vivo metabolism to liberate the amidine moiety and a metabolite (structure 4IV in the FIG. 1). Besides CB$_1$R antagonism, both intact compound and its metabolically cleaved amidine moiety were able to inhibit iNOS activity about 48% and 37% at 1 μM concentration in lung homogenates from LPS-treated mouse (FIG. 4). Mice with diet-induced obesity (DIO) mice were orally treated for 14 days with the compound 2 (10 mg/kg/day). The results are shown in FIGS. 5A-5G. The compound 2 reduced body weight (FIG. 5A), food intake (FIG. 5B), hyperleptinemia (FIG. 5C), hepatic TG (FIG. 5D) and abrogated HFD-induced glucose intolerance (FIG. 5E), insulin resistance (FIG. 5F), and hyperinsulinemia (FIG. 5G). Data represent mean±SEM from 5-6 mice per group. *(P<0.05), indicate significant difference from (STD) diet control. $^\#$indicates significant treatment effect (P<0.05) relative to vehicle-treated HFD group. Food intake was reduced by ~20% during the first week and body weight was progressively reduced by ~10% relative to vehicle-treated DIO mice, but remained significantly higher than the weight of lean mice on regular diet. Glucose tolerance and insulin sensitivity were determined on the last 2 days of treatment, using i.p. glucose tolerance and insulin sensitivity tests. DIO mice show glucose intolerance (blood glucose following an i.p. glucose load of 1.5 g/kg rises higher and takes longer to return to baseline than in lean mice) and insulin resistance (reduction of blood glucose by insulin is attenuated). In compound 2-treated DIO mice, both of these parameters were nearly completely normalized.

Figure 6C:
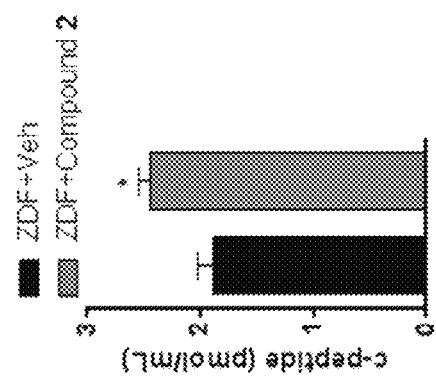
FIGS. 6A-6C show anti-diabetic effect of a compound disclosed herein. ZDF rats were treated with vehicle or compound 2 (10 mg/kg/day) by oral gavage for 7 days. Treatment with compound 2 prevented the progressive increase in blood glucose (FIG. 6A), and parallel decrease in plasma insulin (FIG. 6B), and plasma c-peptide (FIG. 6C). Data represent mean±SEM from 4-5 mice per group. *(P<0.05), indicate significant difference from vehicle group.
Figure 6B:
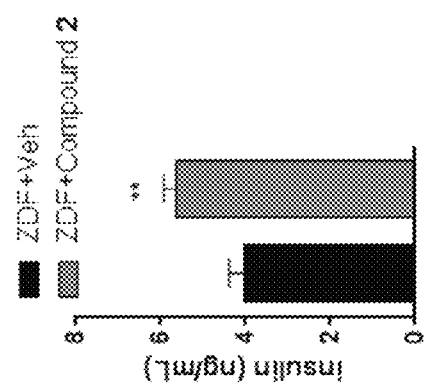
Figure 6A:
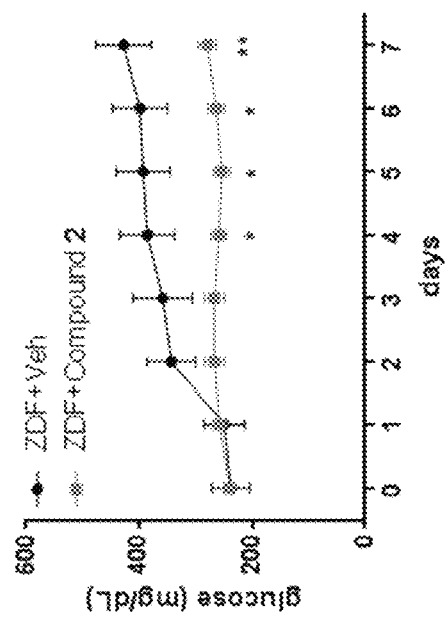

The Zucker diabetic fatty (ZDF) rat is a commonly used animal model of type 2 diabetes with progressive β-cell loss resulting in extreme hyperglycemia. Recently, we showed that peripheral CB$_1$R antagonism prevents β-cell loss by blocking CB$_1$R in infiltrating, proinflammatory macrophages. (Jourdan et al, Nature Med 2013, 19-(9):1132-1140). This highlights the therapeutic potential of peripheral CB$_1$R antagonists in type 2 diabetes. The compound 2 prevented the increase in blood glucose, and the parallel decline in insulin and c-peptide levels in ZDF rats (FIG. 6) which indicates prevention of β-cell loss as reported recently (Jourdan et al, Nature Med 2013, 19-(9):1132-1140).

Figure 7A:
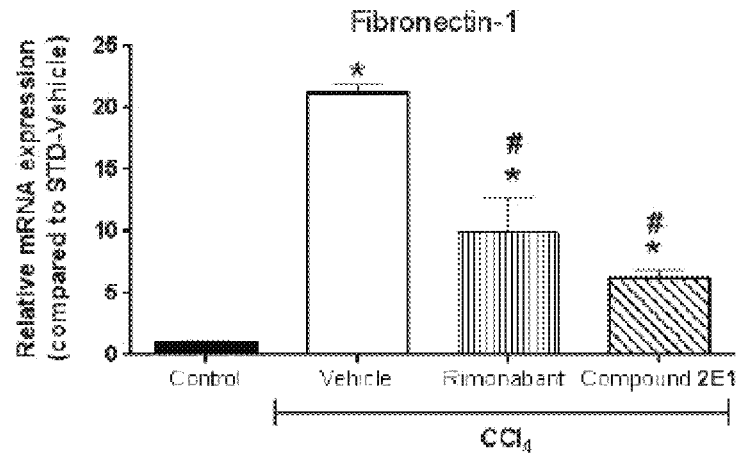
FIGS. 7A-E show anti-fibrotic effect of a compound disclosed herein. $CCl_4$-induced liver fibrosis was generated by intraperitoneal injection of $CCL_4$ (1 ml/kg, diluted 1:10 corn oil), twice weekly for 8 weeks. Mice were also treated with vehicle, rimonabant, or compound 2 at 10 mg/kg/day orally for 4 weeks. Note that compound 2 is more effective than rimonabant in reducing α-SMA (FIG. 7A), Procollagen-1 (FIG. 7B) and Fibronectin-1 mRNA (FIG. 7C) and in reducing liver fibrosis as assessed by Sirius Red and Masson's trichrome staining (FIG. 7D). $CCl_4$-induced increase in immunoreactive iNOS was attenuated by compound 2 but not by rimonabant (FIG. 7E). Data represent mean±SEM from 7-8 mice per group. *P<0.05 relative to control. #indicates significant treatment effect (P<0.05) relative to $CCl_4$-treated vehicle group.
Figure 7B:
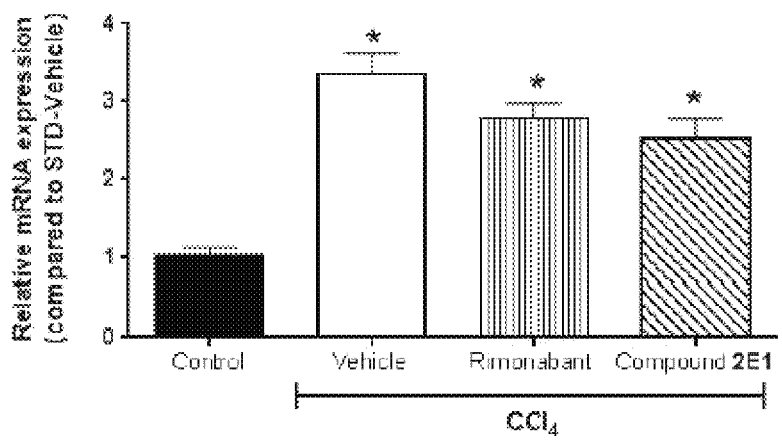
Figure 7C:
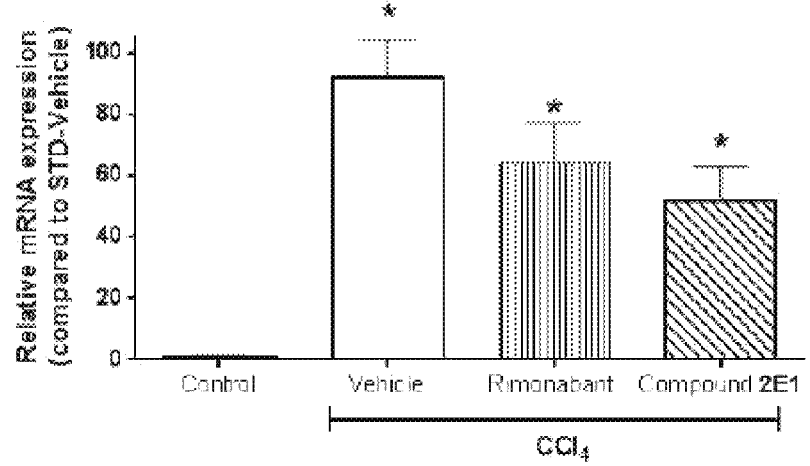
Figure 7D:
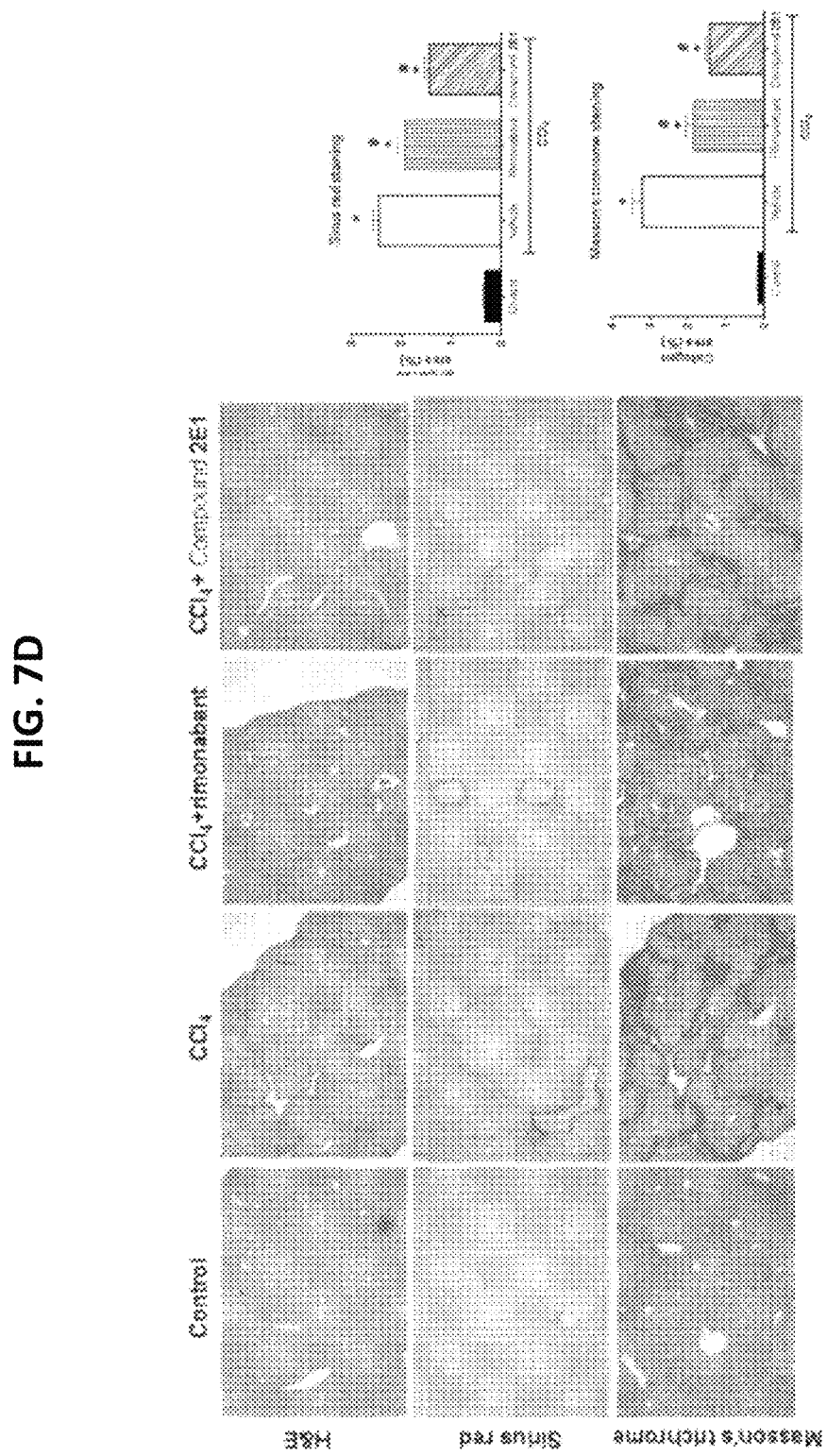
Figure 7E:
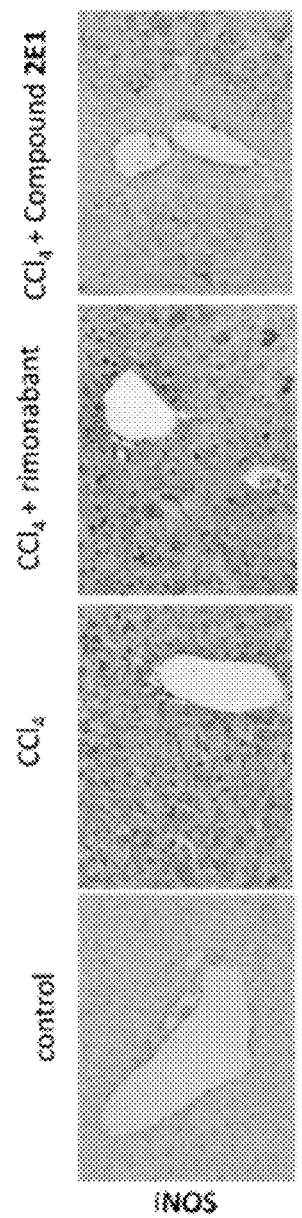

Fibrosis results from excessive extracellular matrix deposition by myofibroblasts accompanying chronic inflammation and wound healing, and is a key pathogenic process in many organs, including kidneys, lung, and liver. Since the prototype CB$_1$R antagonist rimonabant was reported to have an anti-fibrotic effect in mouse models of liver fibrosis (Teixeira-Clerc, Nature Med 2006 12(6); 671-676) we also used CCl$_4$-induced liver fibrosis model in mice to assess the in vivo efficacy of compound 2. In order to compare its efficacy with that of rimonabant, we treated mice either with rimonabant or compound 2E1 (FIG. 7). Compound 2E1 was more effective than rimonabant in reducing CCl$_4$-induced collagen deposition in liver as shown by Sirius red and Masson's trichrome stainings (FIG. 7B,D). Importantly, CCl$_4$-induced elevation of iNOS immunostaining was dramatically attenuated by the compound 2E1 but not by rimonabant (FIG. 7C). This may indicate that dual targeting on CB$_1$R and iNOS by compound 2E1 results in higher in vivo efficacy. Overall, compound 2E1 showed higher anti-fibrotic efficacy than rimonabant in liver fibrosis.

Figure 8:
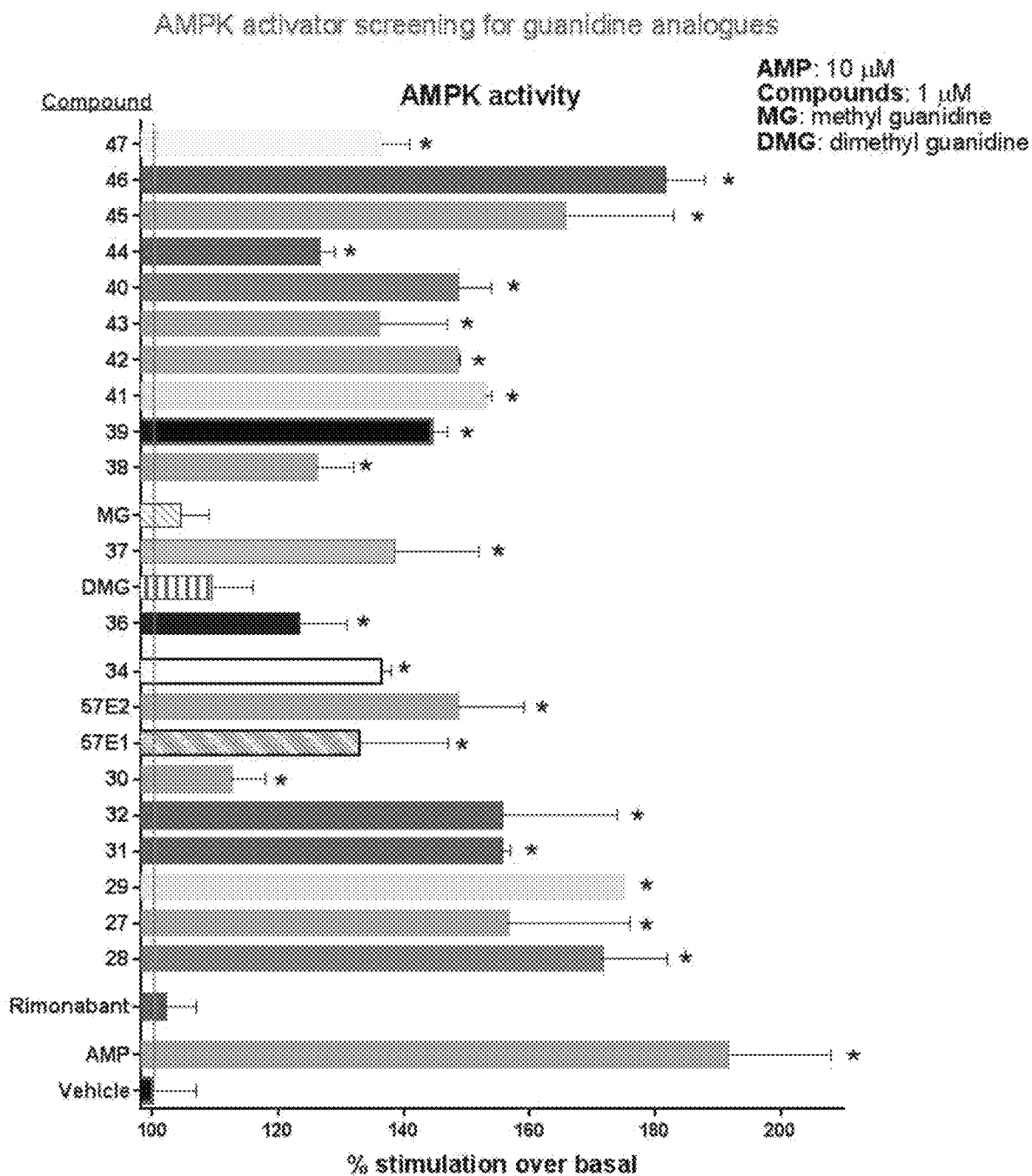
FIG. 8 shows AMPK (AMP-activated protein kinase) activation by compounds disclosed herein. Guanides and biguanides, such as metformin, are effective as antidiabetic agents linked to their AMPK activating properties (Hardie et al., Chem Biol. 2012, 19(1); 1222-1236). Guanidine-containing analogs in certain embodiments were screened for activation of recombinant human AMPK, using an assay kit (Cyclex, Nagona, Japan), as illustrated in FIG. 8. Note that all analogs elicited variable level of AMPK activation, whereas rimonabant even at the high concentration of 1 µM had no effect on AMPK activity.

Activators of AMP-activated protein kinase (AMPK), such as guanidines of biguanides such as metformin are useful for the treatment of diabetes owing to their AMPK activating property (Hardie, et al., Chem & Biol 2012, 19(10); 1222-1236). Guanidine analogues of certain embodiments were screened for AMPK activation by using a recombinant AMPK activity assay. The compounds activated AMPK to various extents, whereas rimonabant had no effect on AMPK activity at 1 μM (FIG. 8).

In view of the many possible embodiments to which the principles of our invention may be applied, it should be recognized that illustrated embodiments are only examples of the invention and should not be considered a limitation on the scope of the invention.

What is claimed is:

1. A method for treating fibrosis, cirrhosis, or liver cancer in a subject, or reversing insulin resistance in a subject, comprising administering to the subject in need thereof a therapeutically effective amount of a compound, or a pharmaceutically acceptable salt or ester thereof, having a structure of:

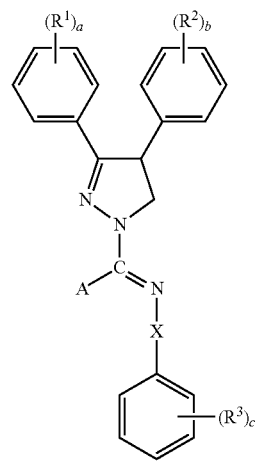

Formula I wherein A is

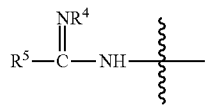

wherein $R^4$ is H, and $R^5$ is $C_1$-$C_6$ alkyl, $C_3$-$C_6$ cycloalkyl, amino, phenyl, heteroaryl, or heterocycloalkyl;

$R^1$, $R^2$, and $R^3$ are each independently selected from optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

X is $SO_2$ or C=O;

$R^{10}$, $R^{11}$, $R^{12}$, $R^{13}$, and $R^{20}$ are each independently selected from H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

$R^{21}$ is optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino;

M is S or Se;

a, b, and c are each independently 0, 1, 2, 3, 4 or 5;

m, x, and y are each independently 0, 1, 2, 3, 4, 5 or 6;

d is 0 or 1; and z is 1 or 2.

2. The method of claim 1, comprising treating fibrosis in a subject.

3. The method of claim 2, wherein the fibrosis is liver fibrosis.

4. The method of claim 1, comprising treating liver cancer in a subject.

5. The method of claim 1, wherein X is $SO_2$, a and c are each one, and b is zero.

6. A method for treating fibrosis, cirrhosis, liver cancer, obesity, diabetes, non-alcoholic and alcoholic fatty liver disease, a co-morbidity of obesity, dyslipidemias that predispose to arteriosclerotic heart disease, diabetic nephropathy, or gout in a subject, or reversing insulin resistance in a subject, comprising administering to the subject in need thereof a therapeutically effective amount of a compound, or a pharmaceutically acceptable salt or ester thereof, having a structure of:

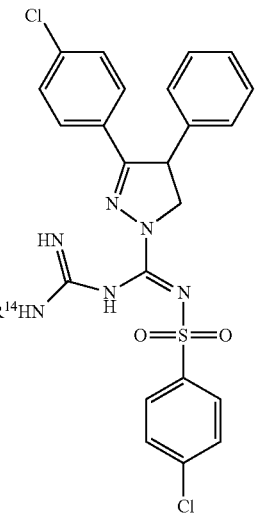

wherein $R^{14}$ is H, optionally-substituted alkyl, optionally-substituted cycloalkyl, halogen, cyano, nitro, hydroxy, optionally-substituted alkoxy, amino, optionally-substituted sulfonyl, optionally-substituted aryl, optionally-substituted heteroaryl, optionally-substituted carboxyl, acyl, optionally-substituted alkenyl, optionally-substituted alkynyl, optionally-substituted phosphonyl, optionally-substituted phosphinyl, optionally-substituted boronate, optionally-substituted silyl, or imino.

7. The method of claim 6, wherein $R^{14}$ is amino.

8. The method of claim 6, comprising treating obesity in the subject.

9. The method of claim 6, comprising treating diabetes in the subject.

10. A method for treating fibrosis, cirrhosis, liver cancer, obesity, diabetes, non-alcoholic and alcoholic fatty liver disease, a co-morbidity of obesity, dyslipidemias that predispose to arteriosclerotic heart disease, diabetic nephropathy, or gout in a subject, or reversing insulin resistance in a subject, comprising administering to the subject in need thereof a therapeutically effective amount of a compound, or a pharmaceutically acceptable salt or ester thereof, having a structure of:

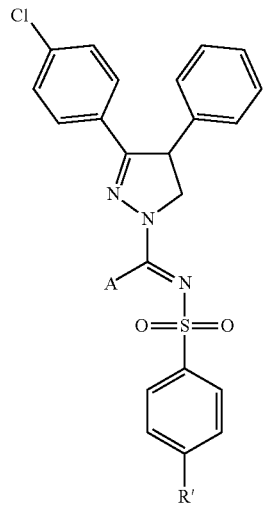

wherein A is NH—C(=NH)—CH$_3$ or NH—C(=NH)—NH—C(=O)—CH$_3$; and

R' is C$_1$ or CF$_3$.

11. The method of claim 10, wherein A is —NH—C(=NH)—CH$_3$ and R' is CF$_3$.

12. The method of claim 10, wherein A is —NH—C(=NH)—NH—C(=O)—CH$_3$ and R' is C$_1$.

13. The method of claim 10, wherein A is —NH—C(=NH)—NH—C(=O)—CH$_3$ and R' is CF$_3$.

14. The method of claim 10, comprising treating obesity in the subject.

15. The method of claim 10, comprising treating diabetes in the subject.

16. The method of claim 11, comprising treating obesity in the subject.

17. The method of claim 11, comprising treating diabetes in the subject.

18. The method of claim 12, comprising treating obesity in the subject.

19. The method of claim 12, comprising treating diabetes in the subject.

20. The method of claim 13, comprising treating obesity in the subject.

21. The method of claim 13, comprising treating diabetes in the subject.

* * * * *